(12) United States Patent
Brosens et al.

(10) Patent No.: US 6,293,952 B1
(45) Date of Patent: Sep. 25, 2001

(54) MEDICAL INSTRUMENT SYSTEM FOR PIERCING THROUGH TISSUE

(75) Inventors: Ivo Brosens, Heverlee; Stefan Gordts, Kessel-Lo; Rudi Campo, Rotselaar, all of (BE); Richard P. Muller, Bronx, NY (US); Frank D'Amelio, Boelton, CA (US); Raymond Ainger, III, Bethel, CT (US); Gregory S. Konstorum, Stamford, CT (US); Michael H. Redler, Ansonia, CT (US)

(73) Assignee: Circon Corporation, Goleta, CA (US)

( * ) Notice: Subject to any disclaimer, the term of this patent is extended or adjusted under 35 U.S.C. 154(b) by 0 days.

(21) Appl. No.: 09/106,675

(22) Filed: Jun. 29, 1998

Related U.S. Application Data

(60) Provisional application No. 60/062,536, filed on Oct. 17, 1997.

Foreign Application Priority Data

Jul. 31, 1997 (BE) .................................................. 09700651

(51) Int. Cl.⁷ .................................................. A61B 17/42
(52) U.S. Cl. ...................................... 606/119; 604/164.01
(58) Field of Search .................................... 606/119, 120, 606/121, 122, 123, 124, 125, 126; 604/164, 165, 104, 158, 161, 170

(56) References Cited

U.S. PATENT DOCUMENTS

| | | | |
|---|---|---|---|
| 341,142 | * 5/1886 | Hamilton et al. | 604/40 |
| 2,705,949 | 4/1955 | Silverman . | |
| 3,330,268 | * 7/1967 | Goldsmith | 600/566 |
| 3,469,580 | * 9/1969 | Huddy | 604/158 |
| 3,698,396 | * 10/1972 | Katerndahl et al. | 604/164 |
| 4,610,663 | * 9/1986 | Rosenberg | 604/99 |
| 4,686,966 | * 8/1987 | Tsai | 600/222 |
| 4,787,892 | * 11/1988 | Rosenberg | 604/170 |
| 4,966,130 | * 10/1990 | Montaldi | 128/17 |
| 4,981,482 | * 1/1991 | Ichikawa | 606/108 |
| 5,098,388 | * 3/1992 | Kulkashi et al. | 604/158 |
| 5,188,630 | * 2/1993 | Christoudias | 606/1 |
| 5,232,442 | 8/1993 | Johnson et al. . | |
| 5,250,036 | 10/1993 | Farivar . | |
| 5,273,545 | 12/1993 | Hunt et al. . | |
| 5,370,623 | 12/1994 | Kreamer . | |
| 5,373,855 | * 12/1994 | Skrabal et al. | 128/750 |
| 5,380,291 | * 1/1995 | Kaali | 604/164 |
| 5,406,939 | * 4/1995 | Bala | 128/4 |
| 5,454,790 | * 10/1995 | Dubrul | 604/104 |
| 5,681,325 | 10/1997 | Hasson | 606/119 |
| 5,685,856 | 11/1997 | Lehrer . | |
| 5,840,077 | * 11/1998 | Rowden et al. | 606/112 |
| 6,080,102 | * 6/2000 | Konou et al. | 600/114 |

OTHER PUBLICATIONS

1. "Clyman Pan–Culdoscope" National Catalog, pp. 34–35.
2. "The Decker Culdoscope" ACMI Catalog, pp. 234–235.
3. Advertisement, InnerDyne Step System, 2 pages, Sep. 1997.
4. "Culdoscopy for the Diagnosis of Obscure Pelvic Disease" by Decker, pp. 5–13, 1965.

* cited by examiner

Primary Examiner—Paul J. Hirsch
Assistant Examiner—Michael B. Priddy
(74) Attorney, Agent, or Firm—Perman & Green, LLP

(57) ABSTRACT

A medical instrument comprising a Veress needle, a dilating obturator, and a cannula. The Veress needle has a tubular safety obturator with an opening in its front section at a needle tip of the Veress needle. A guide with a guide slot can be positioned in a patient's vagina against the posterior fornix of the vagina to guide the Veress needle through the vaginal and peritoneal walls. A guide wire may be passed through the Veress needle and through the hole in the peritoneum wall formed by the Veress needle to guide the dilating obturator through the hole.

25 Claims, 23 Drawing Sheets

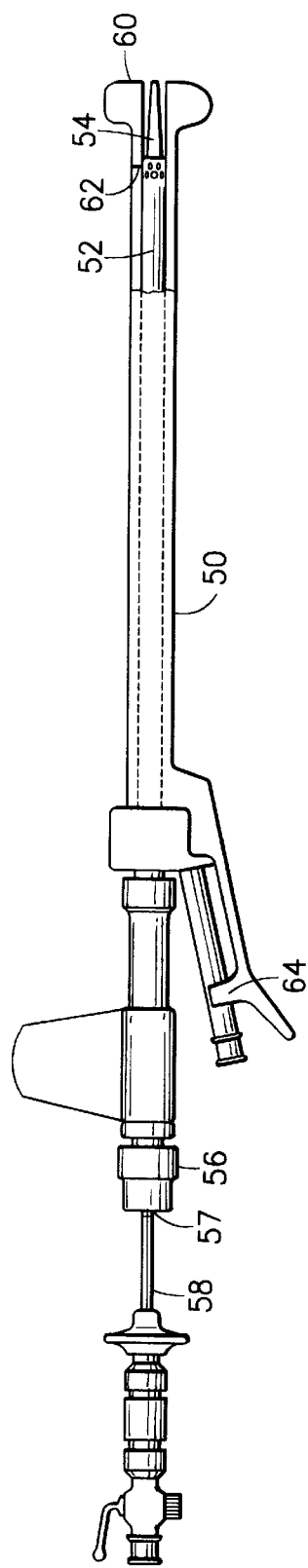
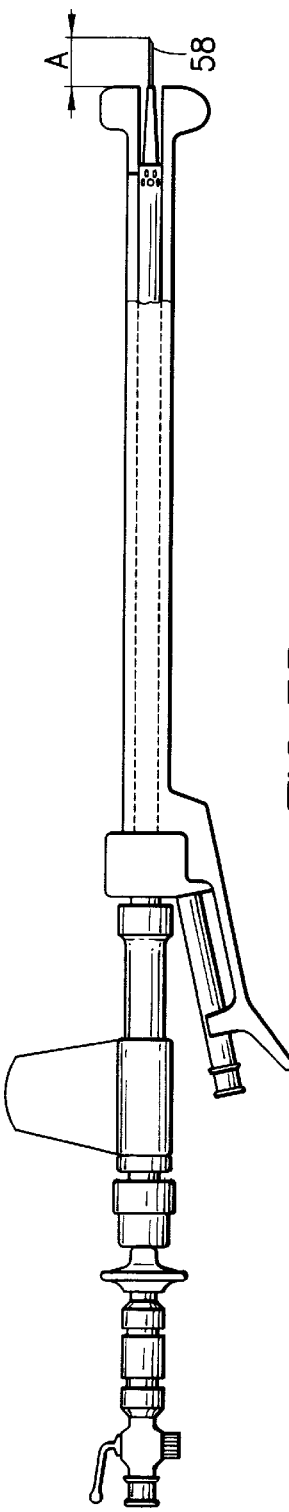
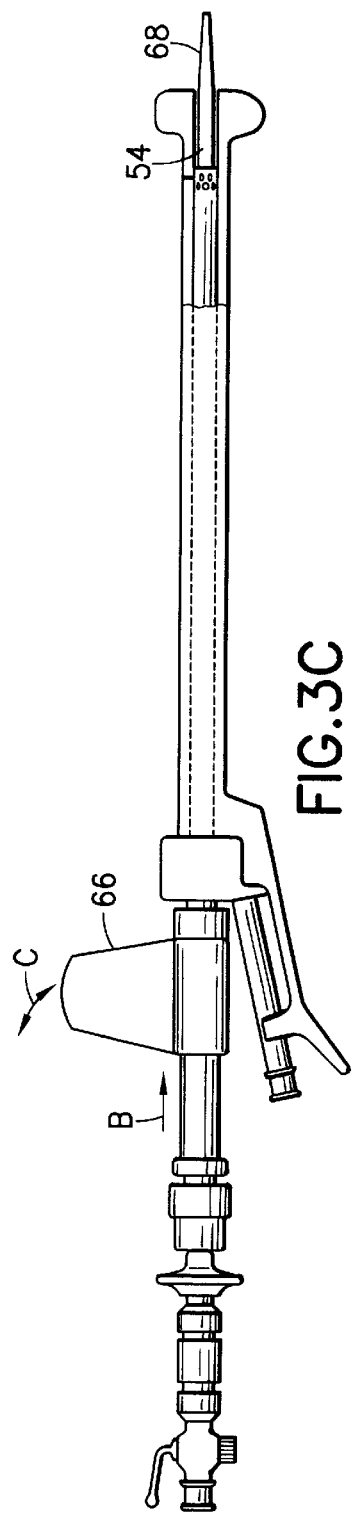
FIG.3A
FIG.3B
FIG.3C

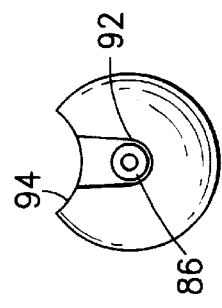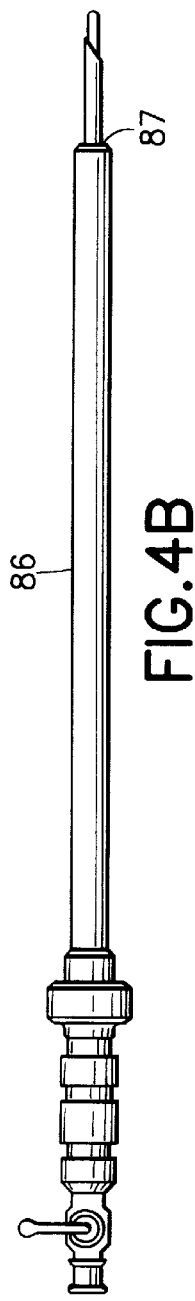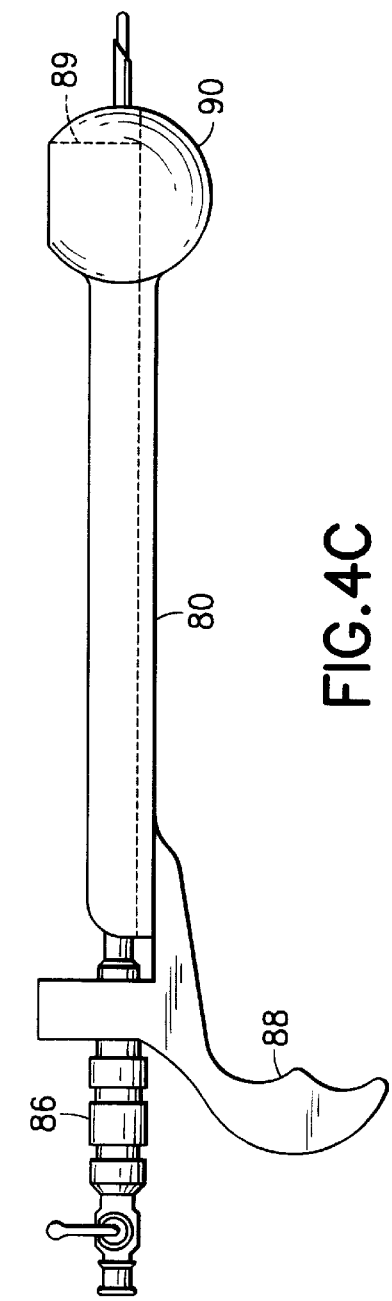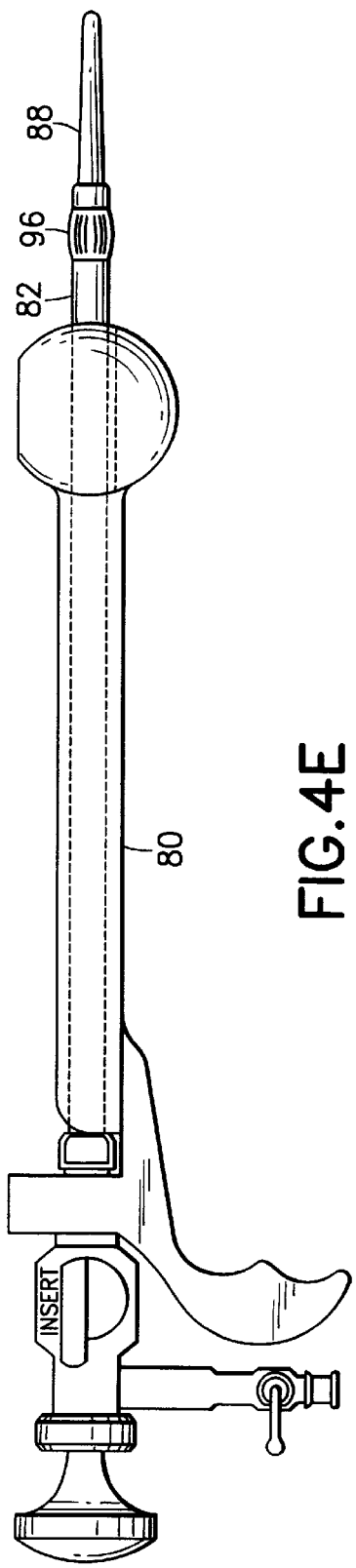

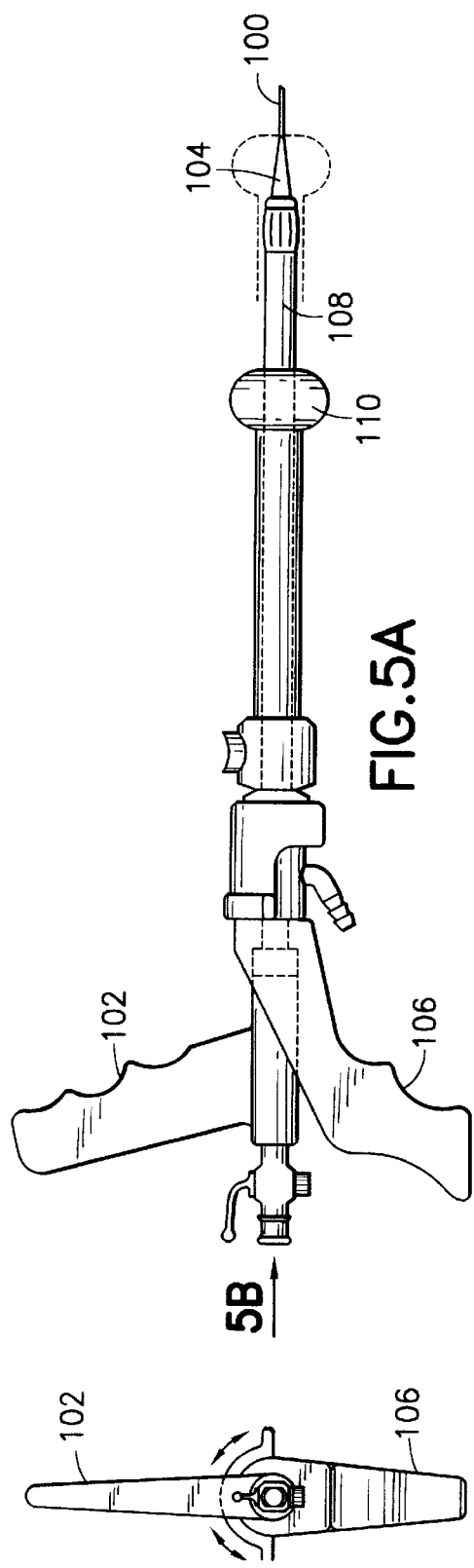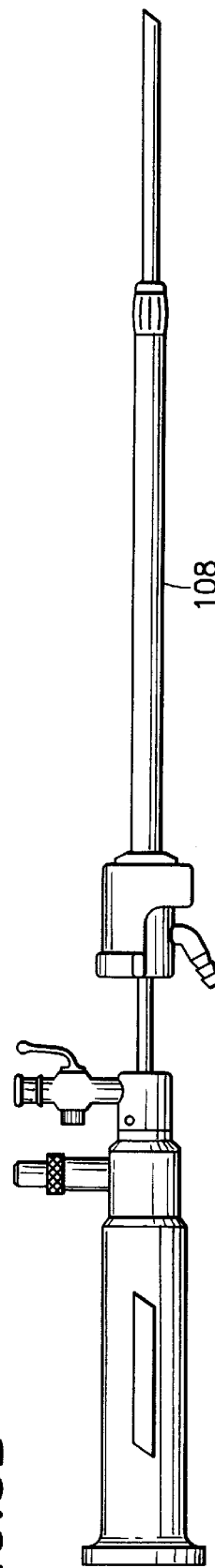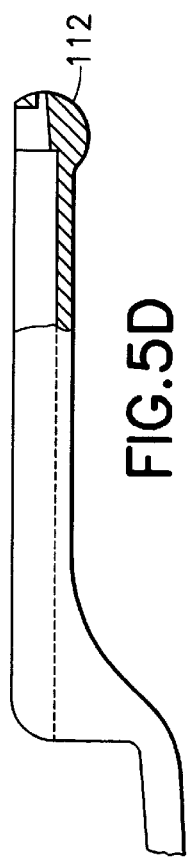

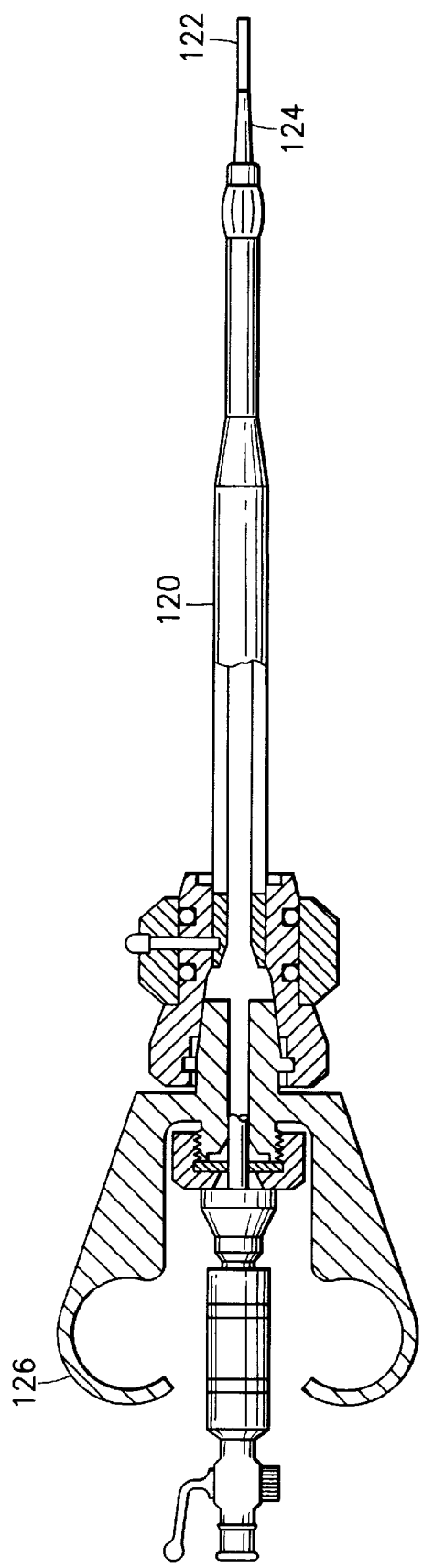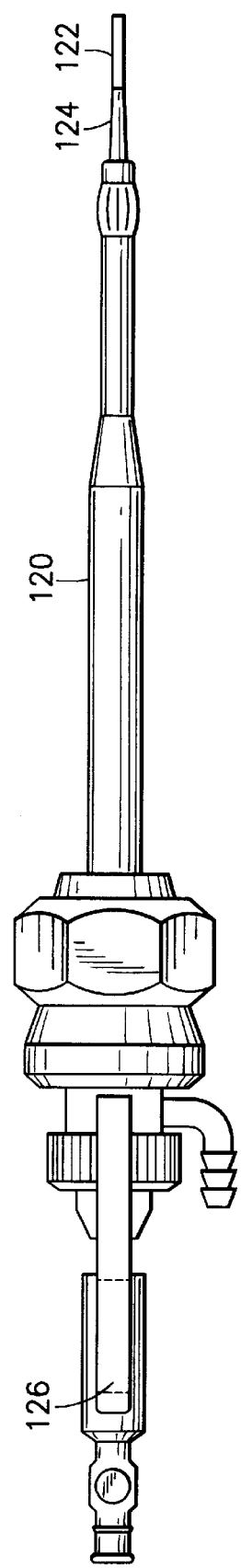

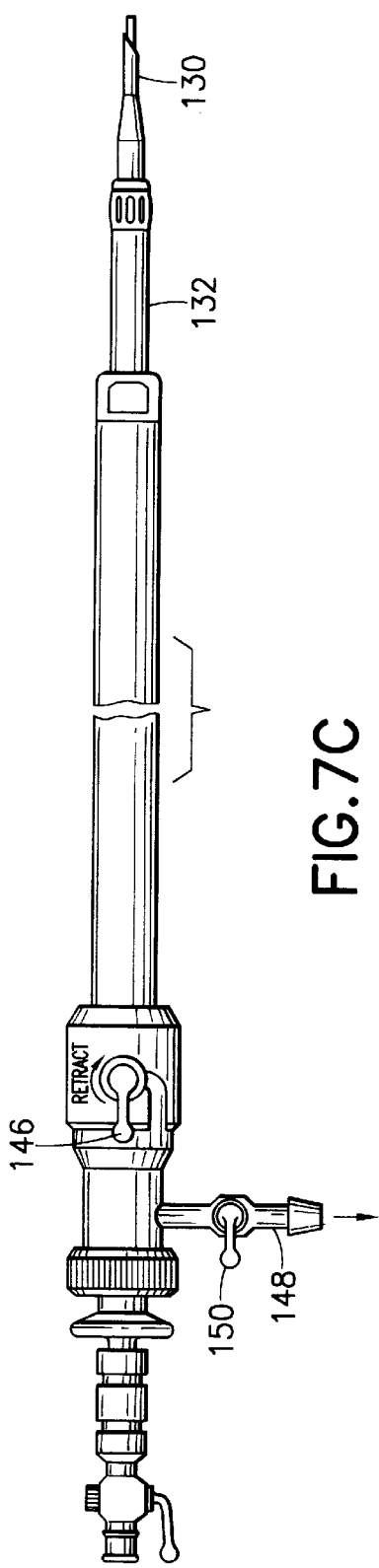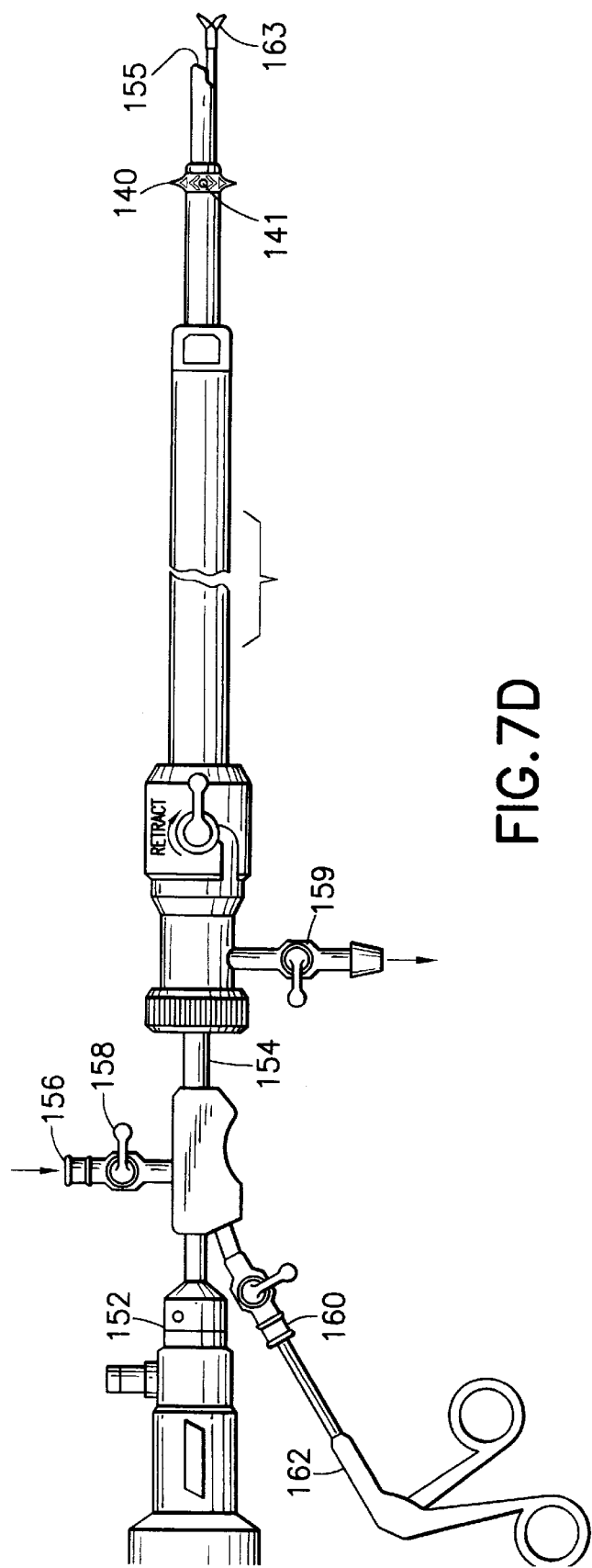
FIG.7C
FIG.7D

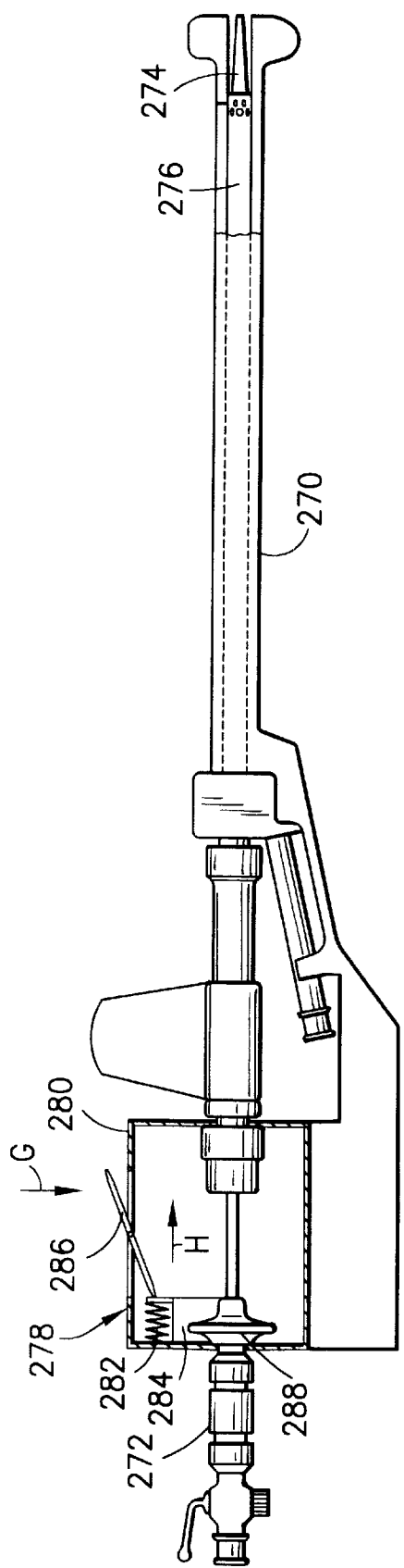
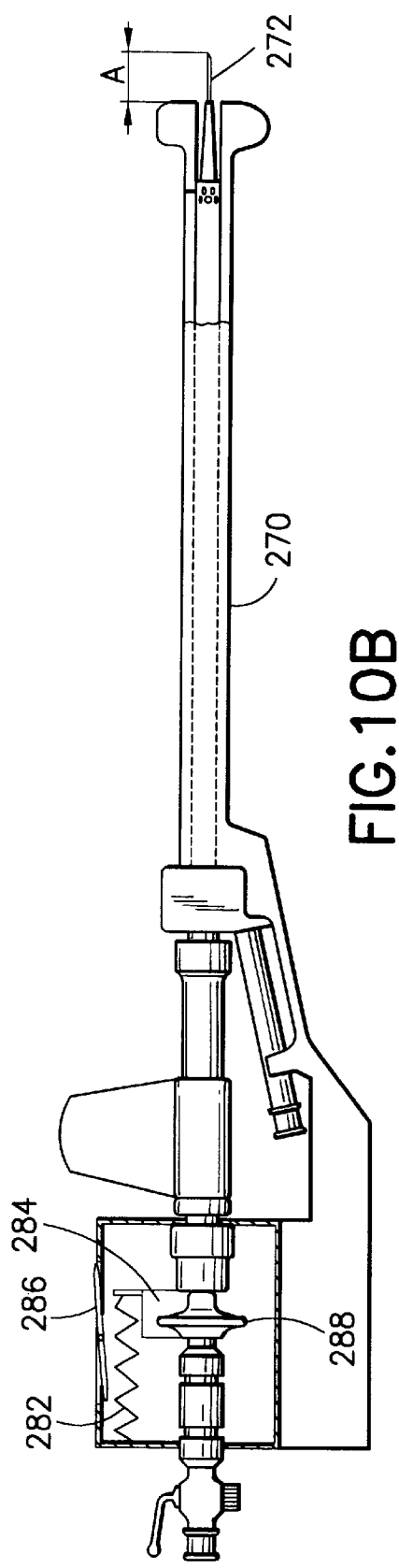

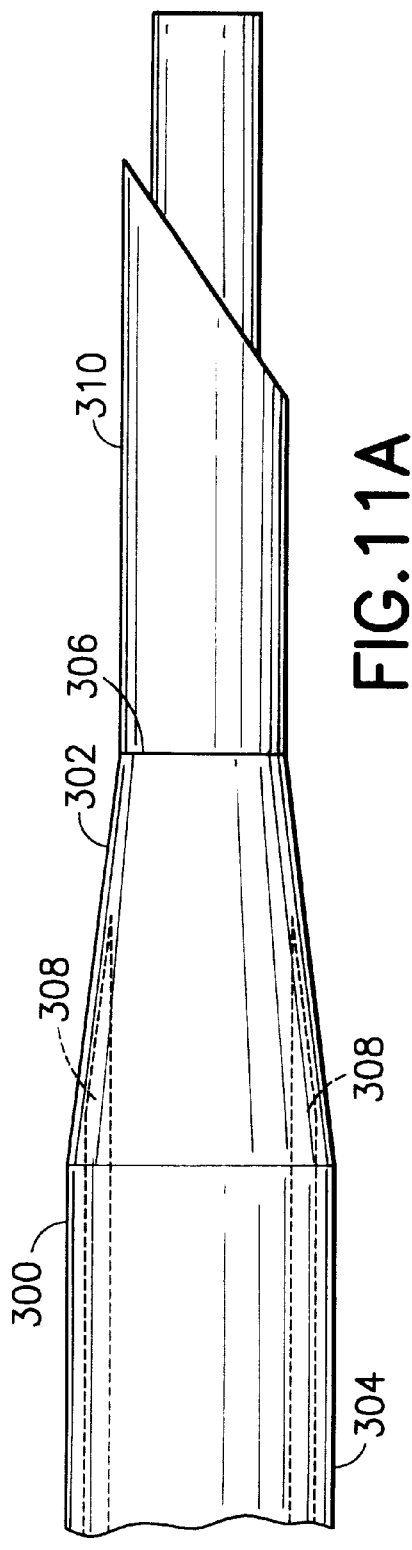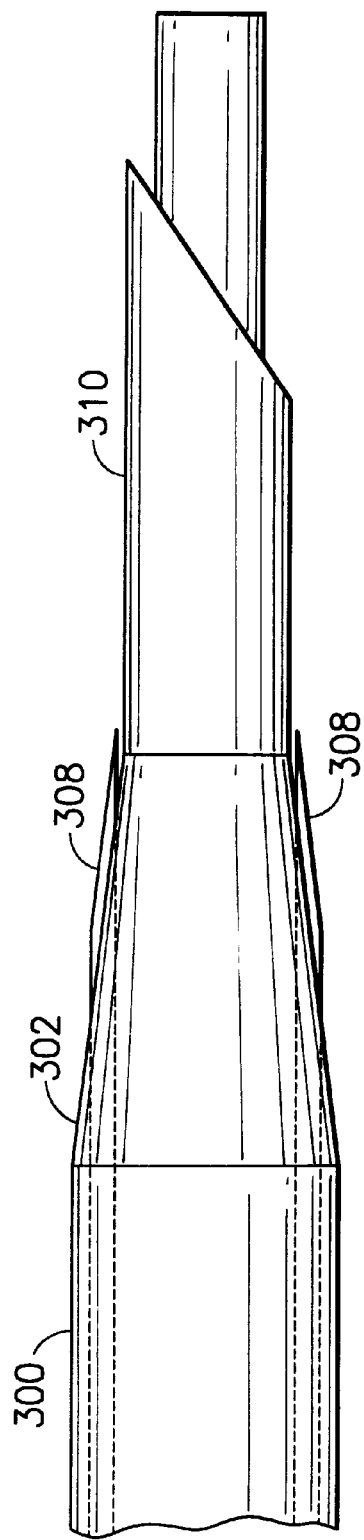

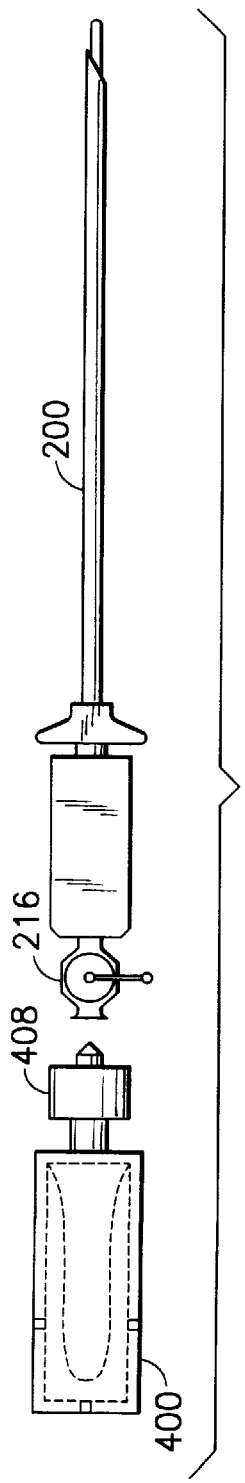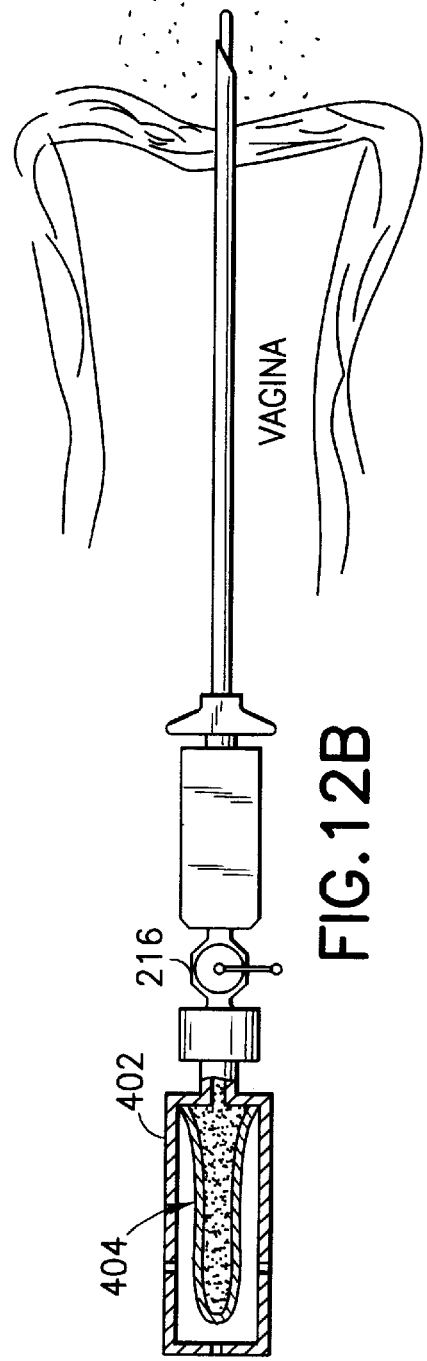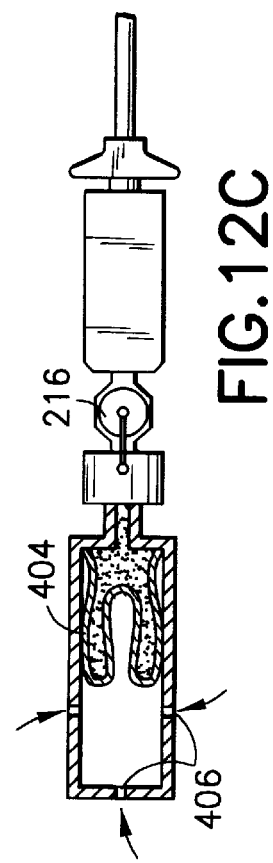
FIG. 12A
FIG. 12B
FIG. 12C

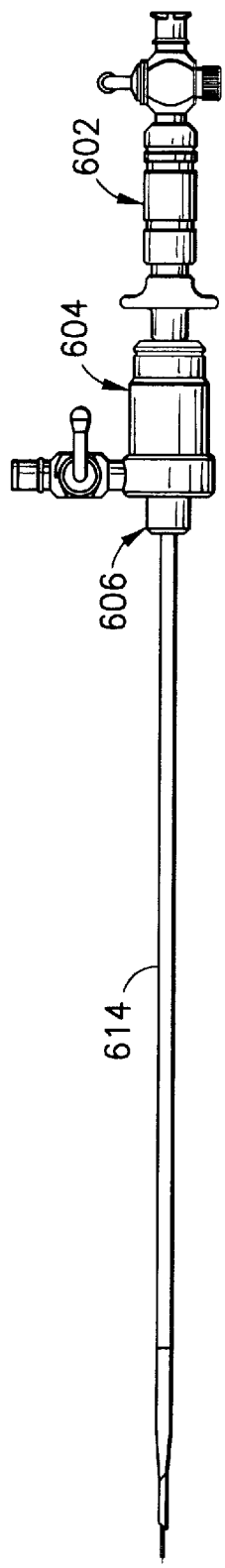
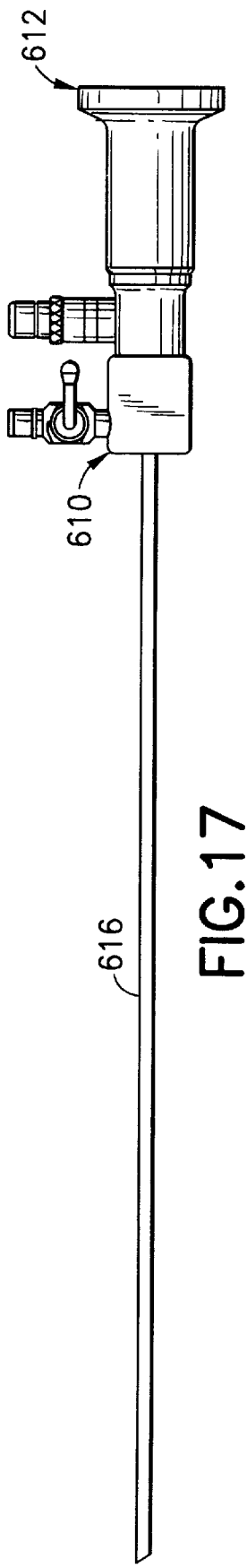

MEDICAL INSTRUMENT SYSTEM FOR PIERCING THROUGH TISSUE

CROSS-REFERENCE TO RELATED APPLICATION

This application claims the benefit of U.S. Provisional Application No. 60/062,536 filed Oct. 17, 1997.

BACKGROUND OF THE INVENTION

1. Field of the Invention

The present invention relates to medical instruments and, in particular, a system and method for placing a cannula through tissue.

2. Prior Art

Culdoscopy is a well known medical procedure for visualization of the pelvic organs by means of an optical instrument through the vaginal route. In the past a relatively large trocar was used to pierce through the peritoneum wall. However, because of the close proximity of the colon and the uterus and because of the relatively large size of the trocar, a surgeon could inadvertently penetrate into or damage the uterus or colon. Precise positioning of the trocar was not always consistent. The present invention is intended to overcome these problems and provide an easier to use and more consistently precise system.

Culdoscopy was abandoned in the 1970s as laparoscopy provided a panoramic view of the pelvis and was shown to be superior for tubal sterilization. Difficulties and complications of culdoscopic sterilization were, however, associated with visualization and exteriorisation of the tube. The advantages of culdoscopy in infertility were stressed in the French and English literature. While the technology of laparoscopy was continuously improved the technique of culdoscopy did not advance after the 1960s.

Diagnostic laparoscopy as a standard procedure in the investigation of infertility is frequently performed in healthy women without obvious pelvic pathology resulting in normal findings or pathology of doubtful clinical significance. Unfortunately, laparoscopy is not innocuous and should be considered as a major surgical procedure. For these reasons the procedure is frequently postponed in asymptomatic patients until a later stage in the investigation process, and repeat procedures to evaluate the evolution of disease or to check the effect of treatment are not considered routine clinical practice. Minilaparoscopy is likely to be more acceptable by avoiding general anesthesia. However, the access from the umbilicus used in laparoscopy does not give the ideal angle for inspecting the tubo-ovarian structures. To expose the full ovarian surface and fossa ovarica several steps are required such as Trendelenburg position, distension by $CO_2$ pneumoperitoneum, insertion of a second trocar and manipulation of bowel and adnexa. The $CO_2$ pneumoperitoneum provokes patient's discomfort and the acidosis is potentially harmful to the patient and, where intrafallopian transfer procedures are involved, to gametes and embryos. Concern has also been expressed that growth and spread of tumor cells may be accelerated by laparoscopy with air or $CO_2$. Finally, structures such as fimbriae and avascular adhesions are easier to inspect by hydroflotation than with a pneumoperitoneum. The use of saline as the distension medium in diagnostic laparoscopy is attractive but impracticable with the patient in the Trendelenburg position.

SUMMARY OF THE INVENTION

Unlike culdoscopy used in the past, a patient undergoing minihydroculdoscopy in accordance with the present invention can be positioned in a lithotomy position on her back; not in a knee-chest position as in the old style culdoscopy. This has the advantage of less risk of the patient falling off of the examining table. Unlike culdoscopy used in the past which required relatively large patient sedation because of the pain from use of a large trocar, minihydroculdoscopy in accordance with the present invention can be used with only local anesthesia because only a small puncture hole is pierced and then expanded in a less painful manner than merely puncturing a large size hole. Puncturing a relatively large size hole used in culdoscopy in the past required larger force than with puncturing the relatively small size hole with the present invention. Thus, the present invention provides less risk that the needle will travel too far past the peritoneum wall after puncture occurs. In addition, unlike culdoscopy used in the past with the patient in the knee-chest position, minihydroculdoscopy in accordance with the present invention allows the doctor to view the patient's body behind the peritoneum wall in a more readily recognizable position. Thus, less orientation confusion occurs to the doctor.

In accordance with one embodiment of the present invention, a medical instrument guide is provided comprising a leading end, a shaft and a rear end. The leading end has a general ball shape and a guide channel therethrough. The leading end is sized and shaped to seat in a vagina against a peritoneum wall of a patient. The shaft extends from the leading end. The rear end is connected to the shaft and is sized and shaped to be held and manipulated by a user. The guide can be inserted into the patient's vagina and positioned against the peritoneum wall such that a medical instrument can be inserted through the guide channel to a position against the peritoneum wall below the patient's uterus.

In accordance with another embodiment of the present invention, a Veress needle assembly is provided comprising a tubular needle shaft, and a tubular obturator. The tubular needle shaft has a needle tip. The tubular obturator is slidably located inside the needle shaft and has an open front end. The obturator has an extended position with its front end in front of the needle tip of the needle shaft and a retracted position with its front end located behind the needle tip. The obturator forms a channel therethrough to pass an article out the open front end.

In accordance with another embodiment of the present invention, a medical instrument system is provided comprising a cannula, a dilating obturator, a first Veress needle assembly and a second Veress needle assembly. The dilating obturator is located inside the cannula. The first Veress needle assembly has a first tubular needle shaft and a first needle tip obturator slidably located in the first needle shaft with a closed blunt front end. The second Veress needle assembly has a second tubular needle shaft and a second needle tip obturator slidably located in the second needle shaft with a tubular shape having an open front end. The first and second Veress needle assemblies are alternatively slidably located in the dilating obturator.

In accordance with another embodiment of the present invention, a medical instrument is provided for piercing through tissue. The instrument comprises a Veress needle and a positioner. The positioner has a locator section sized and shaped to be inserted in a vagina of a patient and located against a peritoneum wall of the patient. The positioner has the Veress needle movably mounted thereto. The positioner further comprises means for moving the Veress needle forward on the positioner a predetermined limited longitudinal distance from a home position on the positioner.

In accordance with another embodiment of the present invention, a medical instrument is provided for piercing through tissue. The instrument comprises a Veress needle assembly and a dilating obturator. The dilating obturator has the Veress needle assembly slidably connected thereto. The dilating obturator has retractable laterally extending cutting blades at a front end thereof.

In accordance with another embodiment of the present invention, a medical instrument for access through tissue is provided comprising a cannula and a combined Veress needle and dilator assembly. The combined Veress needle and dilator assembly has a one-piece tube shaped frame piece with a needle tip section and a dilating outwardly expanding section behind the needle tip section. The combined Veress needle and dilator assembly further comprises a spring loaded safety obturator located at the needle tip section. The one-piece frame piece of the combined Veress needle and dilator assembly is adapted to both pierce a small hole through tissue and expand the hole in the tissue to about the same size as the cannula.

In accordance with another embodiment of the present invention, a Veress needle assembly is provided comprising a frame and a pressure signaler. The frame has a general tubular shape with a center channel, a needle shaped open front end, and an open rear end into the center channel. The pressure signaler is connected to the open rear end. The pressure signaler is adapted to signal a user of the difference in gas pressure at the open front end relative to atmospheric pressure.

In accordance with one method of the present invention, a method of inserting a cannula through a peritoneum wall of a patient is provided comprising steps of inserting a Veress needle assembly into a vagina of the patient and through the peritoneum wall to form a hole in the peritoneum wall; expanding the size of the hole; and sliding the cannula into the expanded size hole.

BRIEF DESCRIPTION OF THE DRAWINGS

The foregoing aspects and other features of the invention are explained in the following description, taken in connection with the accompanying drawings, wherein:

FIGS. 3A–3F are elevational side views of another embodiment of the present invention at various configurations during use;

FIGS. 4A–4H are elevational side views of another alternate embodiment of the present invention;

FIGS. 5A–5D show another alternate embodiment;

FIGS. 6A and 6B show another alternate embodiment;

FIG. 7C shows the components of FIGS. 7A and 7B configured as introduced into the peritoneum;

FIG. 7D shows the operating configuration of the cannula/retractor shown in FIG. 7C in use with a telescope and an accessory device;

FIGS. 10A and 10B are side views of an alternate embodiment of an instrument with a needle projection mechanism;

FIGS. 11A and 11B are partial side views of the front of an instrument having a Veress needle assembly and a dilating obturator with movable cutting blades;

FIGS. 12A, 12B and 12C show a Veress needle assembly in use with a pressure signaler;

FIG. 16 is an elevational side view of an assembly of the Veress needle, obturator and cannula shown in FIG. 15;

FIG. 17 is an elevational side view of an assembly of the sheath and telescope shown in FIG. 15;

DETAILED DESCRIPTION OF THE PREFERRED EMBODIMENTS

Figure 1:
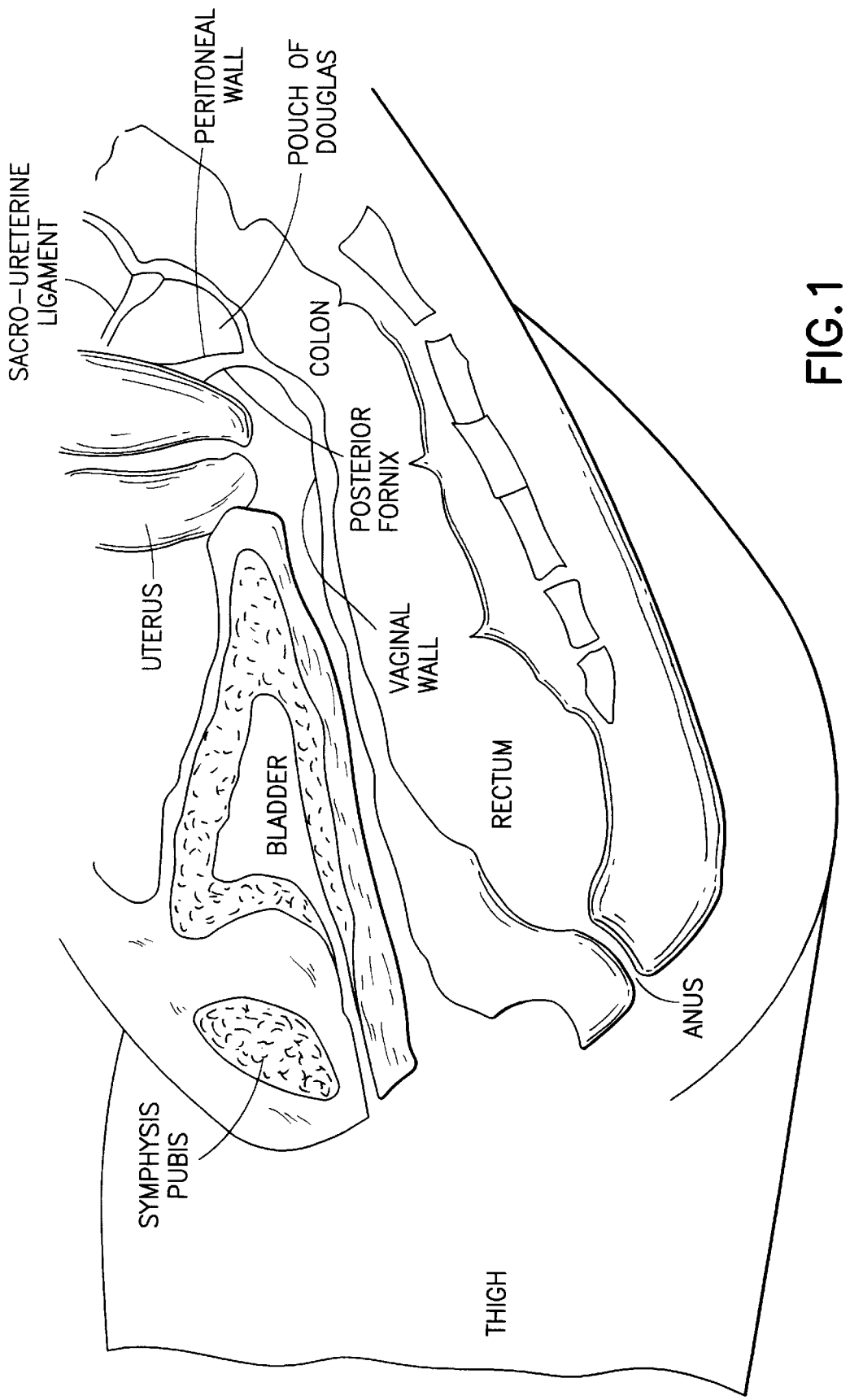
FIG. 1 is a schematic cross-sectional view of a portion of a human female body.

FIG. 1 shows a portion of the female human anatomy. Located at the inner end of the vagina is the peritoneum wall. The colon curves upward from below this area and the uterus is located above this area as shown.

The present invention relates to a new technique, which is referred to herein as minihydroculdoscopy. Minihydroculdoscopy is for the exploration of the tubo-ovarian structures in infertile patients without obvious pelvic pathology. It aims to be an acceptable alternative to diagnostic laparoscopy; a standard but not innocuous procedure which infrequently reveals pathology in the asymptomatic patient. Minihydroculdoscopy is performed under local anesthesia using a small diameter optic with the patient in dorsal position. Cavity distension is achieved with normal saline. Minihydroculdoscopy does not provide the familiar and panoramic view of the pelvis given by laparoscopy, but does have several advantages. This includes accurate and atraumatic inspection of adnexal structures without manipulation and with opportunity to perform dye hydrotubation and salpingoscopy. The risks of a general anesthetic are avoided. There is also less risk of trauma to major vessels. The high patient acceptability makes minihydroculdoscopy suitable as an early stage procedure in the investigation of infertility and as a repeat or second look procedure. Minor operative procedures such as biopsy and adhesiolysis can also be performed. In patients with obvious pelvic pathology, diagnostic laparoscopy will obviously remain the procedure of choice. Minihydroculdoscopy deserves full evaluation of its accuracy, risks and benefits before it can be accepted as a new first line technique in gynecological practice.

Figure 2A:
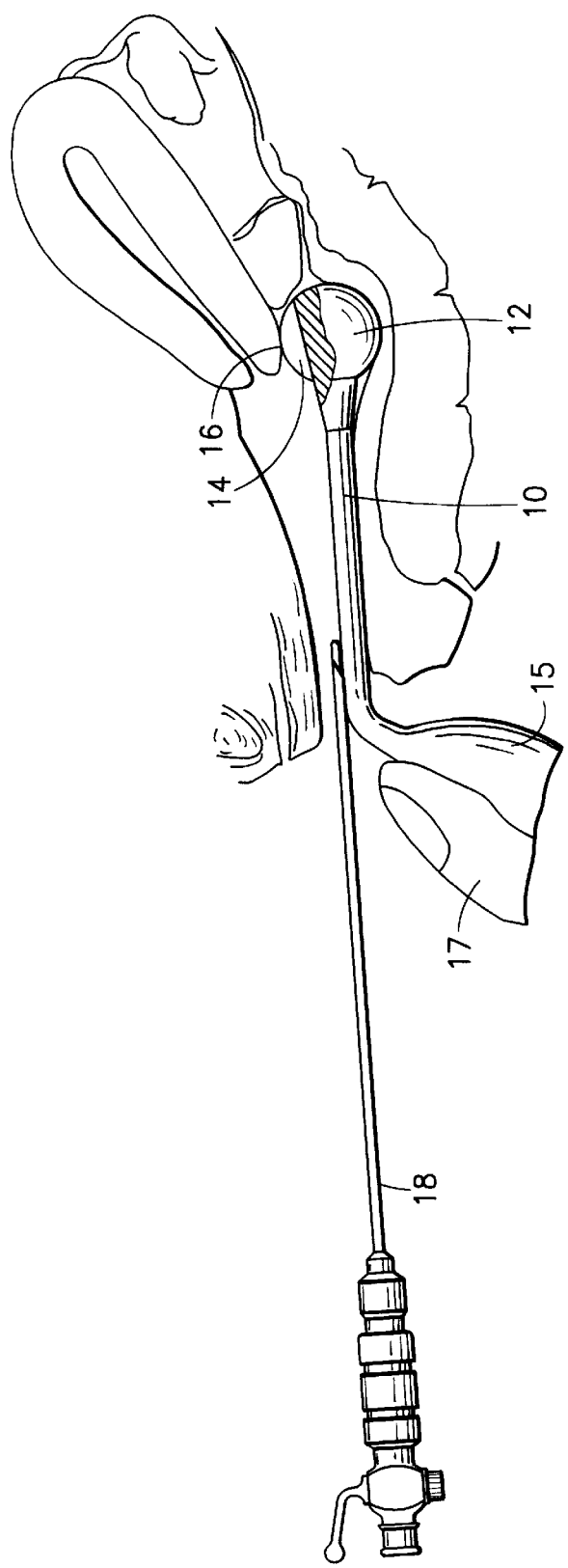
FIGS. 2A–2E are schematic views of a system incorporating features of the present invention in use with a patient.
Figure 2B:
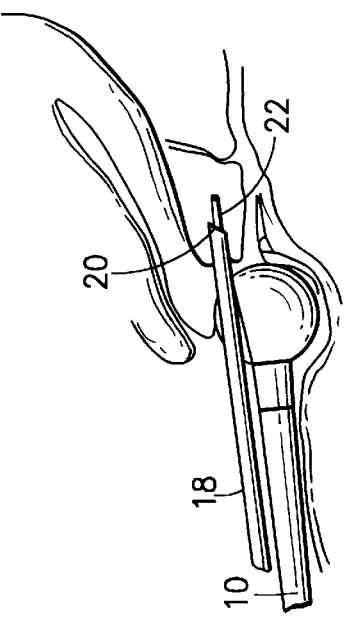
Figure 2C:
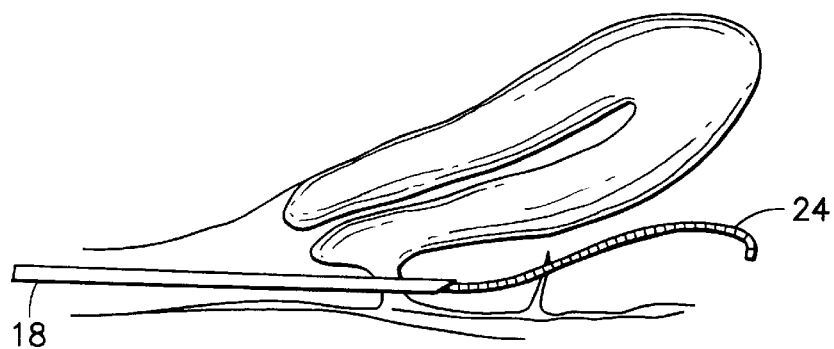
Figure 2D:
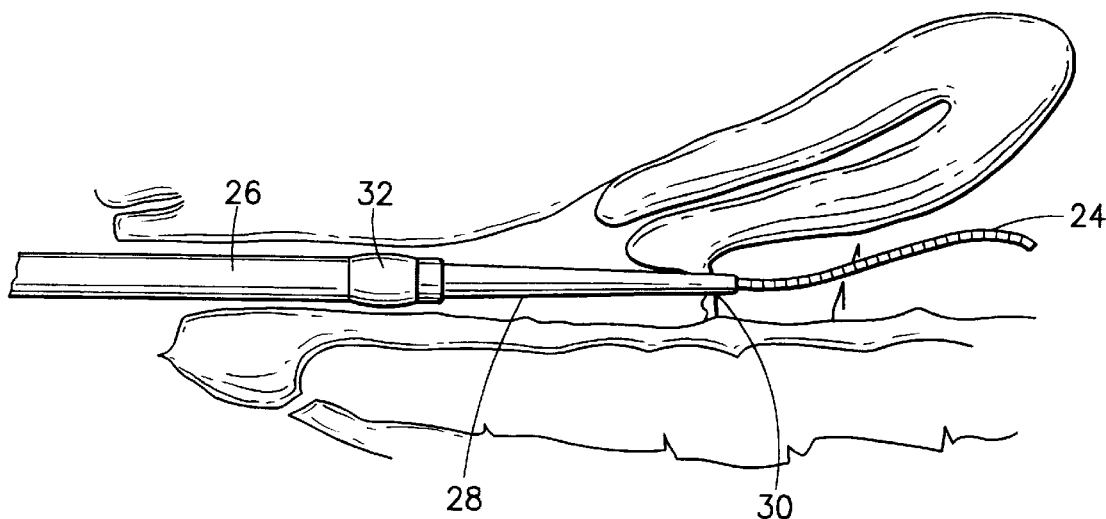
Figure 2E:
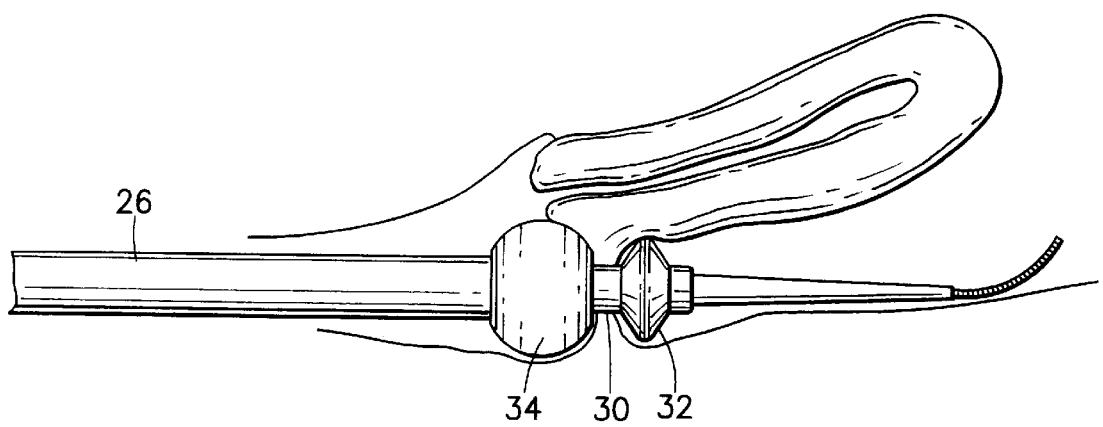

Referring also to FIGS. 2A–2E, the minihydroculdoscopy procedure and some of the tools that can be used to perform the procedure will be described. First, a guide 10 is inserted into the vagina. The leading end 12 of the guide is positioned against the peritoneum wall. The leading end 12 is sized and shaped to seat fairly well in this area. In the embodiment shown the leading end 12 has a general ball or ellipsoid shape with a diameter of about 15 mm–25 mm and with a guide channel 14. The top 16 of the leading end 12 preferably has a flat or concave shape to accommodate the cervix in this area. A rear end 15 of the guide 10 is located outside the patient and can be grasped by the surgeon's fingers 17 to manipulate and hold the guide steady. However, the shape of the leading end 12 relative to the shape of the tissue in front of the wall, makes proper positioning of the leading end 12 very accurate and relatively simple. In alternate embodiments the leading end of the guide could have any general rounded, conical or circular shape to preferably cause the tissue at the posterior fornix to be tightened. By tightening this tissue, penetration with the Veress needle can be done easier, faster and less painful. The surgeon then inserts the leading end of the Veress needle 18 into the vagina and into the guide channel 14. Veress needles are generally well known in the art. As described herein, an old style Veress needle can be used or a new style could be used and may have various different new features. However, in a basic form a Veress needle comprises at least a frame piece with a needle shaped tip and a spring loaded safety obturator section. The present invention could also be used with a needle that did not have a spring loaded safety obturator section; i.e.: not a Veress needle. In one embodiment, the needle 18 is a 115 mm Veress needle but any suitable size Veress needle could be used. The leading end of the Veress needle 18 has a needle tip 20 and a spring loaded obturator section 22, also known as a spring loaded stylet. In this embodiment the obturator section 22 has a closed blunt or rounded front end. When the Veress needle 18 is pushed forward, the obturator section 22 contacts the peritoneum wall and is pushed back into the needle 18 to leave the needle tip 20 at the front which subsequently pierces through the peritoneum wall. Once through the wall, the obturator section 22 springs back to its forward position. This helps to prevent the needle tip 20 from piercing through unintended tissue. In this embodiment, as seen with FIG. 2C, the obturator section is removed and the surgeon inserts a guidewire 24 through the interior of the needle 18. The leading end of the guidewire 24 is inserted past the peritoneum wall. As seen in FIG. 2D, the needle 18 is then removed and a retractor/cannula 26 is then inserted onto the guidewire 24. A tapered or dilating obturator 28 is also provided between the guidewire 24 and the retractor/cannula 26. This arrangement allows the guidewire 24 to guide the leading edge of the tapered obturator 28 precisely into the relatively small puncture hole 30 in the peritoneum wall. The surgeon then pushes the assembly forward with the tapered obturator 28 expanding the size of the hole 30. In a preferred embodiment, the obturator 28 has a lubricious coating thereon to assist in reducing friction and thereby make insertion easier. Coatings could include chromium, TEFLON, a hydrophobic coating, or any other suitable type of coating. In this embodiment, as seen in FIG. 2E, once the retractor section 32 of the retractor/cannula 26 is passed through the hole 30, the retractor section 32 can be expanded to prevent the retractor/cannula 26 from being inadvertently dislodged from the wall. The purpose of the retractor section 32 is, thus, to prevent unintentional or accidental removal of the retractor/cannula 26 out of the hole 30. This is accomplished by expansion of the retractor section 32 to a size larger than the hole 30. In alternate embodiments, different types of retractor sections could be used, such as balloon or umbrella or a series of hinged leaves. However, any suitable type of retractor section could be provided. Alternatively, no retractor section need be provided. An optional safety flange 34 can be used to help prevent any undesired excessive forward movement of the retractor cannula 26. The surgeon can then remove the guidewire 24 and the obturator 28 and subsequently insert an optical viewing device and perhaps a working tool(s) through the cannula 26. In an alternate method, the surgeon does not use the guide 10. Instead, the surgeon uses a tenaculum or forceps to move the cervix and pull the posterior fornix taut. The surgeon then merely places the front end of the Veress needle against the taut posterior fornix and penetrates into the pouch of Douglas. In an alternate embodiment the guide could be part of a vaginal speculum or the tenaculum or forceps. The vaginal speculum could alternatively or additionally have an integrated tenaculum or forceps to move the cervix and pull the posterior fornix taut. Some of these alternative embodiments are described with reference to FIGS. 18–22 below.

Figure 3D:
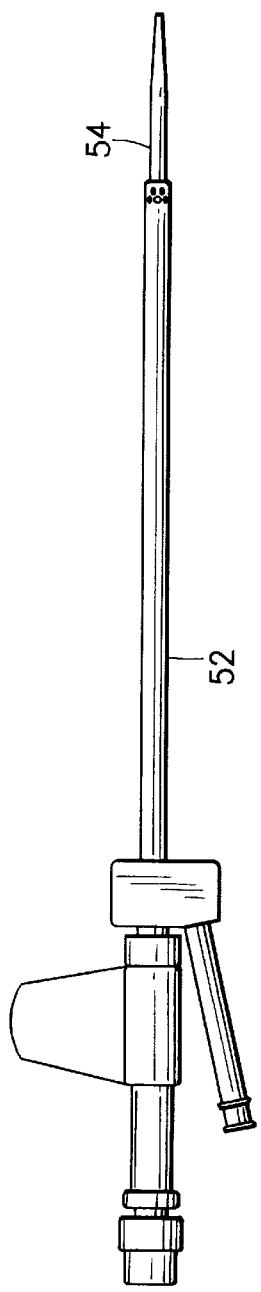
Figure 3E:
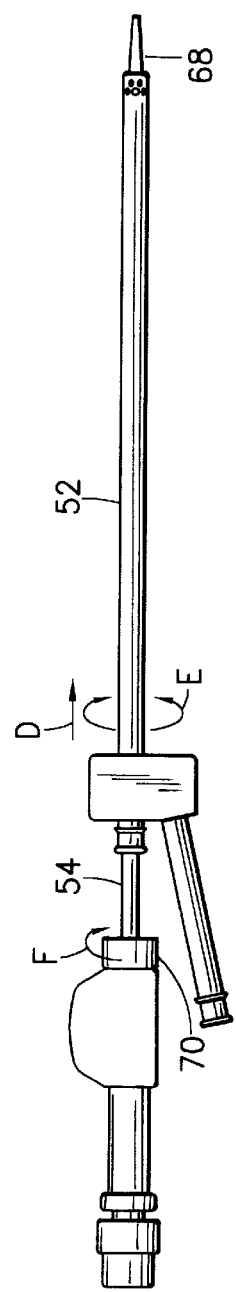
Figure 3F:
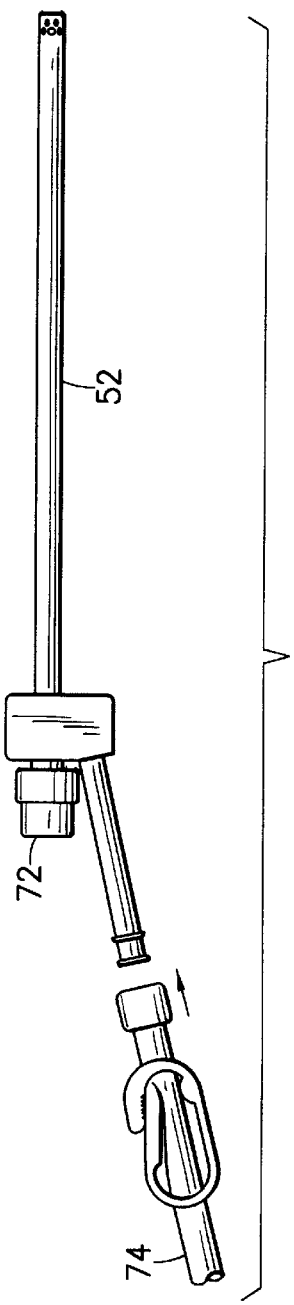

Referring now to FIGS. 3A–3F, another embodiment of the system will be described. The system includes a cervical guide 50, a cannula 52, a dilating obturator 54, a seal 56, and a Veress needle 58. The components form an assembly as shown in FIG. 3A. Once assembled, the leading end 60 of the guide 50 is inserted into position next to the cervix. The obturator 54 and the needle 58 are located in retracted positions relative to the guide 50 behind the front end of the guide. The needle 58 has an indicator mark 57, such as a green strip, which, if visible, signals the surgeon that the needle is in fact retracted behind the leading edge of the guide 50. In this embodiment the guide is removably mounted to the cannula 52 by one or more couplers. The couplers may be in the form of a small front pocket section 62 and a snap-mount rear section 64 attached to a rear irregation post on the cannula 52. Once the assembly is in position, the surgeon then pushes the Veress needle 58 forward. In this embodiment the forward travel distance of the Veress needle 58 is limited to a distance A. The distance A is preferably an amount of penetration that should avoid unintended damage to tissue on the opposite side of the peritoneum wall. A distance of about 15 mm as the distance A should avoid such damage. This punctures the peritoneum wall with a tiny puncture, such as about 1.5 mm in diameter. The surgeon then pushes the obturator 54 forward as seen in FIG. 3C by pushing forward on the obturator torque tab 66 as illustrated by arrow B. While pushing forward with the tab 66, the surgeon also twists the tab 66 as indicated by arrow C to axially rotate the leading edge 68 of the obturator 54. This wedges the leading edge 68 through the hole in the wall thereby enlarging the hole. Once the obturator 54 is fully inserted in the hole, the surgeon can then remove the Veress needle and the guide as illustrated in FIG. 3D. To insert the cannula 52, the surgeon pushes the cannula forward on the obturator 54 as illustrated by arrow D in FIG. 3E while also twisting or axially rotating as illustrated by arrow E. The obturator 54 is then disengaged from the cannula by twisting the lever lock 70 as illustrated by arrow F. Once the obturator 54 is removed, the surgeon can then attach the seal 72 and the outflow tubing 74 to the cannula 52. Subsequently, the surgeon can insert the telescope into the cannula 52. In this embodiment no retractor is provided.

Figure 4A:
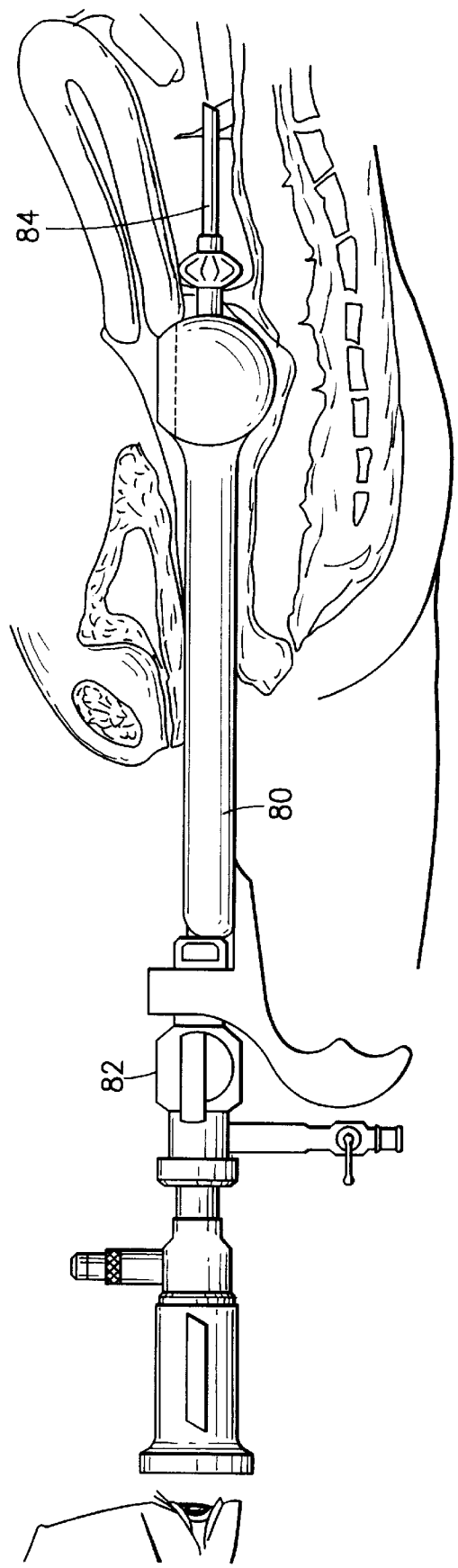
Figure 4F:
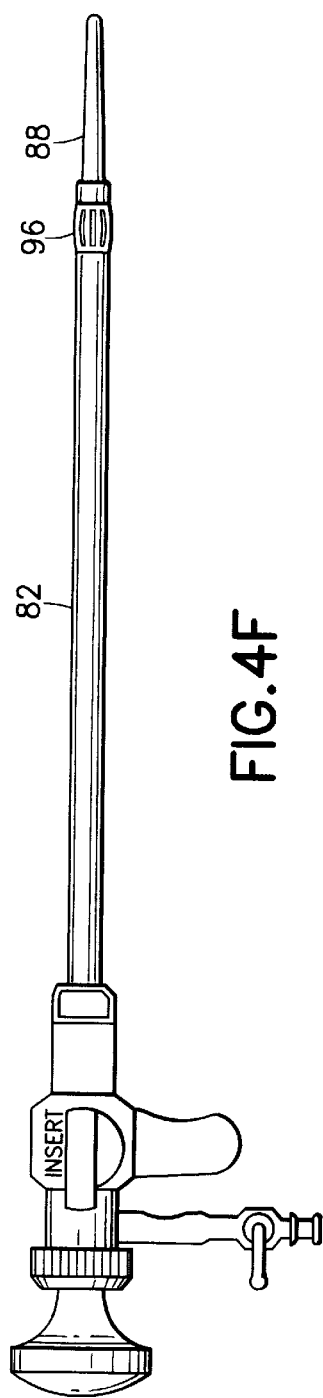
Figure 4G:
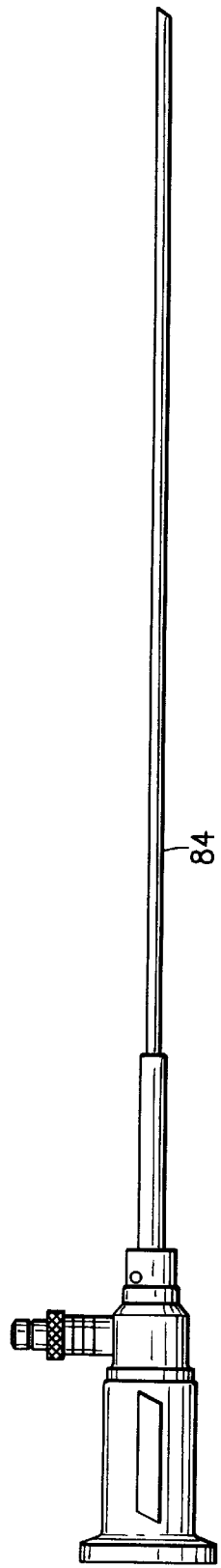
Figure 4H:
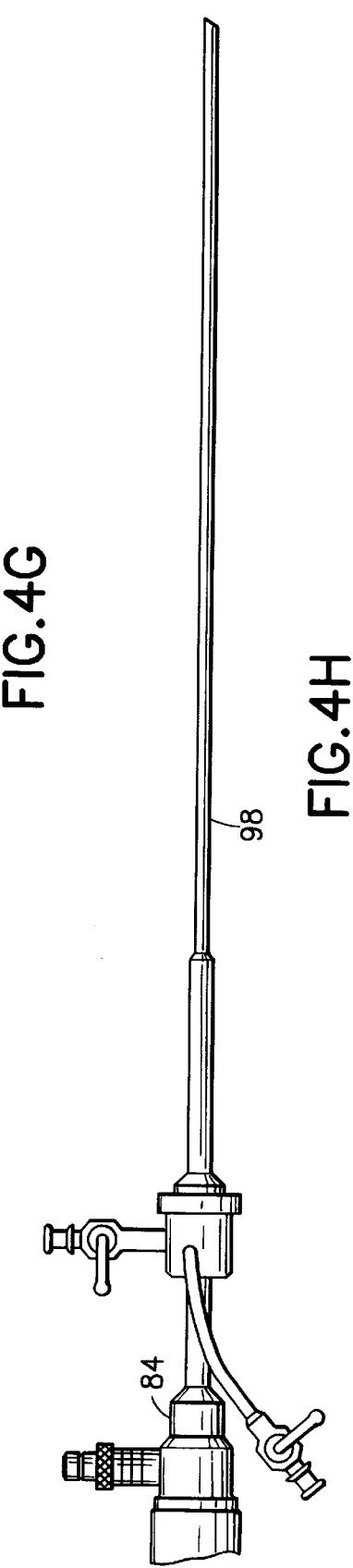

FIG. 4A shows another alternate embodiment of the system in use. The system has a cervical guide 80, a cannula/retractor 82 and the telescope 84. In this embodiment the guide 80 does not detach from the cannula/retractor 82 during use of the telescope 84. FIGS. 4B–4H show various components of the system. FIG. 4B shows the Veress needle 86. The Veress needle 86, in this embodiment, has a front stop ledge 87 that interacts with a stop ledge 89 in the guide leading portion 90 to limit forward movement of the Veress needle 86 relative to the guide 80. The needle 86 snap-lock mounts with the guide 80 as shown in FIG. 4C. The guide 80 has a handle 88 for the surgeon. The leading portion 90 of the guide has a guide channel 92 and a top recess 94 to accommodate the cervix. In this embodiment the top recess 94 has a curvature with a radius of about 17.5 mm. However, any suitable shape and size could be provided. Once the initial hole is formed by the needle 86, the needle 86 is removed from the guide 80 and the obturator 88 and cannula/retractor 82 are then inserted into the guide 80 with the guide remaining in place. The surgeon then pushes the obturator and the cannula/retractor through the hole, expands the retractor section 96, removes the obturator 88, and inserts the telescope 84 (see FIG. 4G). FIG. 4H shows an optional operating hysteroscope sheath 98 connected to the telescope 84.

FIGS. 5A–5C show another alternate embodiment. In this embodiment the Veress needle 100 has a handle 102. The dilating obturator 104 also has a handle 106. The handles allow the surgeon to axially twist the Veress needle and the dilating obturator as they are pushed forward. The cannula/retractor 108 has a non-detachable (except for cleaning) cervical stabilizer 110. In an alternate embodiment the cannula/retractor 108 could be used with the detachable temporary guide 112 shown in FIG. 5D.

FIGS. 6A–6B show another alternate embodiment with a cannula/retractor 120, a Veress needle 122, and a dilating obturator 124. In this embodiment the obturator 124 has a finger grip handle 126 at its rear end. The handle 126 can also help the surgeon push the cannula/retractor 120 into place and help in easier withdrawal of the obturator 124. Thus, one handle can be used to push both the obturator and the cannula/retractor 120 into position.

Figure 7A:
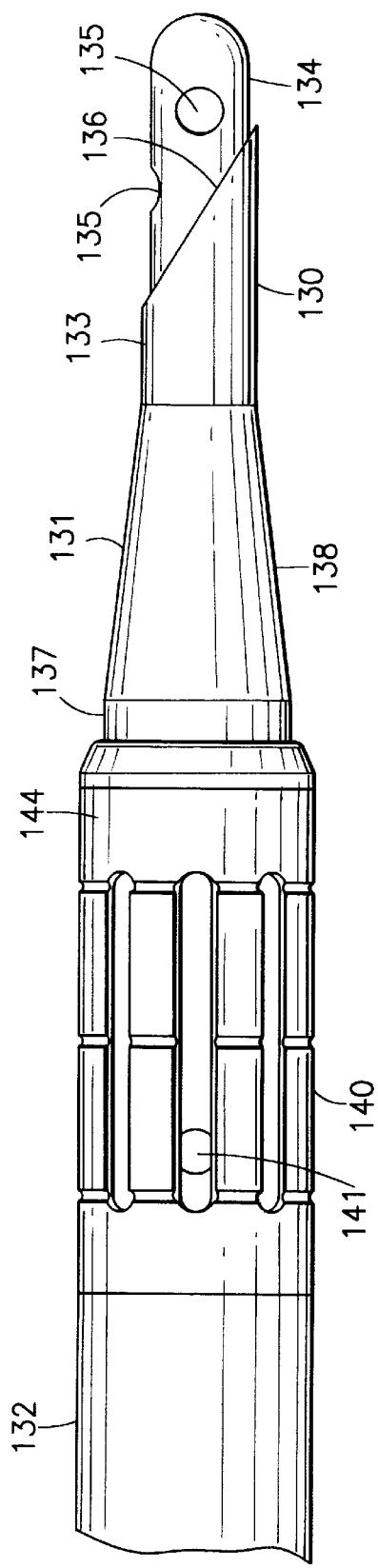
FIGS. 7A and 7B show distal ends of alternate embodiments of the cannula/retractor and a combined Veress needle and dilating obturator.
Figure 7B:
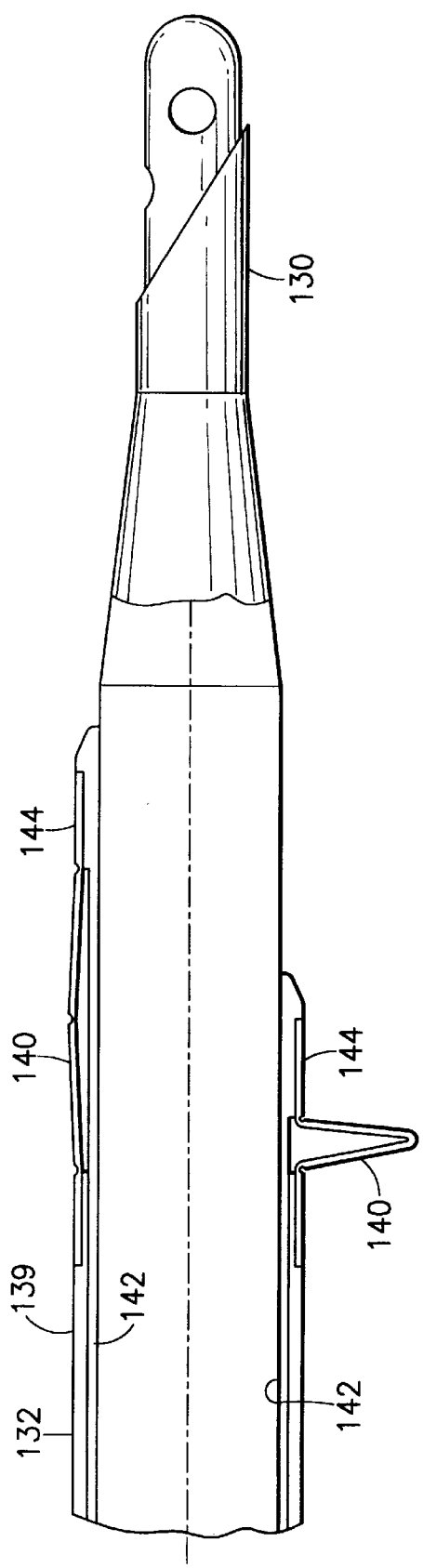

Referring now to FIGS. 7A and 7B, an enlarged view of the distal ends of an obturator/needle 130 and a cannula/retractor 132 are shown. The obturator/needle 130 has a spring loaded safety obturator 134, a needle tip section 136, and a dilating obturator section 138. The safety obturator 134 includes aspirating holes 135. The obturator/needle 130 is an assembly with a tubular one-piece frame piece 131 which has the needle tip section 136. The needle tip section 136 is at a first front section 133 of the frame piece 131 having a first diameter, such as about 1 mm. The frame piece 131 has a second section 137 with a larger second diameter. The dilating obturator section 138 is also formed by the frame piece 131 and is located between the first and second sections 133, 137. The dilating obturator section 138 outwardly expands between the two sections 133, 137 to function as a wedge to enlarge tissue as the frame piece is advanced through a hole formed by the needle tip section 136. Thus, a separate dilating obturator need not be used. The cannula/retractor 132 has a retractor section 140 formed by an outwardly expanding collapsible sleeve. FIG. 7B shows the sleeve in its expanded (see bottom section) and collapsed (see top section) positions. A control 146 (see FIG. 7C) is provided at the proximal end of the cannula/retractor and is connected to the retractor section 140 by a transmission member 142 which is connected to a front cannula section 144. The control 146 can longitudinally move the transmission member 142 back and forth relative to the rigid tubular frame piece 139 of the cannula/retractor 132.

FIG. 7C shows the entire components of FIGS. 7A and 7B. The proximal end of the cannula/retractor 132 has an irrigant outflow 148 with a stopcock 150. FIG. 7D shows the cannula/retractor 132 with the needle/obturator 130 removed and the telescope 152 inserted. In this embodiment a working sheath 154 is provided. The telescope extends through the sheath 154. The proximal end of the sheath has an irrigant inflow 156 with a stopcock 158 and an accessory device inlet 160. Thus, an accessory device, such as forceps 162, can be passed through the sheath 154 to the distal end of the telescope 152. In this embodiment, the cannula/retractor 132 has an outflow stopcock 159 the umbrella type retractor section 140, and inlet holes 141. The inlet holes 141 are located beneath the leaves of the retractor section 140. When the leaves of the retractor section 140 are expanded outward, as shown in FIG. 7D, the retractor section 140 forms a standoff such that tissue does not block the holes 141.

A study was conducted to test the general idea described above. The following is a description of the study:

Technique

A mild rectal laxative was self-administered by the patient the morning of the procedure. Minihydroculdoscopy was performed with the patient in the dorsal decubitus position, positioned so she could follow the procedure on a video screen. After disinfection with aqueous chlorhexidine solution the central part of the posterior fornix was infiltrated with 1–2 ml of 1% lidocaine with adrenaline 1:100,000. In the present preferred method chlorhexidine is no longer used. With a tenaculum placed on the posterior lip, the cervix was lifted and the Veress needle was introduced approximately 1.5 cm below the cervix and tested by deeper insertion for intraperitoneal location. Approximately 100 ml saline solution at 37° C. diluted with 1% lidocaine in a concentration of 1/100 was instilled in the pouch of Douglas. Initially the insertion of a 3 mm blunt trocar was facilitated by a step incision in the posterior fornix. A 2.7 mm diameter semi-rigid endoscope was used with an optical angle of 30° and a flow channel. A 3-chip CCD digital video camera was attached to the endoscope. The endoscope was introduced approximately 1 cm through the trocar sheath into the pouch of Douglas. With the 30° optical angle in the upwards position the posterior wall of the uterus was inspected. Subsequently, by rotation and deeper insertion of the scope the tubo-ovarian structures were seen. The saline irrigation was continued throughout the procedure to keep the bowel and tubo-ovarian structures afloat. At the end of the procedure this fluid, about 400 ml in total, was left in situ, and the instruments removed. The vaginal fornix was left to close spontaneously. When indicated, hysteroscopy was performed to check the uterine cavity. After the procedure patients were informed that some vaginal leakage or bleeding could occur and were advised not to use vaginal tampons and to abstain from intercourse for six days. Prophylactic antibiotics were prescribed for three days in the form of azithramycine 500 mg once daily.

Patient Selection

The technique was explained to 28 patients attending an infertility clinic who had normal findings both on gynecological examination and transvaginal ultrasound scan. Informed consent for the procedure was obtained in all cases. The investigation was performed no earlier than seven days after the onset of menstruation. The purpose of the procedure was to exclude endometriosis and adhesions of the tubo-ovarian structures. In one patient the procedure was used as a second look procedure six months after reconstructive surgery for a right ovarian endometrioma. The first seven patients received a general anesthetic and underwent the miniculdoscopy immediately prior to a diagnostic laparoscopy by the same operator, in order to compare the results.

Results

For the first seven patients, the findings were similar at laparoscopy and at minihydroculdoscopy, but minihydroculdoscopy proved superior at detecting small filmy adhesions. In the group as a whole, access to the pouch of Douglas failed in three patients. The visualization was unilateral in three patients due to extensive adhesions which were confirmed later by laparoscopy. In the other patients the tubo-ovarian structures were clearly visualized on both sides. Moving the endoscope allowed inspection of the distal tubal segment, the ovarian surface and the fossa ovarica without grasping and manipulation of tissues. The fimbriae were inspected in their natural position underlying and embracing the ovary. By moving the optic the folds of the infundiublum were inspected. Tubal patency was tested at the end of the procedure by transcervical dye hydrotubation with methylene blue.

Cannulation of the Fallopian tube with the 2.7 mm scope to inspect the ampullary mucosa (salpingoscopy) was also attempted successfully and proved to be painless.

Ovarian endometriosis, adhesions and small pedunculated fibromas were identified by moving the optic around the ovary. Filmy adhesion-like and fibrotic structures were detected on the ovarian surface while they were floating in saline. Tubo-ovarian adhesions were diagnosed in seven patients and endometriosis in four patients. None of these lesions had been detected by vaginal sonography.

The whole procedure lasted between 20 and 40 minutes. It was tolerated surprisingly well by all patients without any form of analgesia or sedation, and none of the explorations had to be interrupted for pain or discomfort. One patient developed pain at the end of the procedure from hemorrhage at the puncture site. No other complications occurred in this small series. All patients expressed their satisfaction at being able to watch the procedure on the video screen, and none objected having it repeated if indicated.

Discussion

The study has demonstrated the ease of performing minihydroculdoscopy in an outpatient setting. The failure in three patients was largely due to initial technical problems. In one case, excessive injection of local anesthetic at the puncture site caused dissociation of the peritoneum from the posterior fornix. Access to the pouch of Douglas is now performed as a culdocentesis technique with a sharp Veress needle. These results can be compared to a 4% failure rate for classical culdoscopy. Minihydroculdoscopy is less traumatic than diagnostic laparoscopy as transabdominal insertion of the Veress needle and trocars, manipulation of organs, and drying and acidosis of tissues are avoided. Hydroflotation allows inspection of the tubo-ovarian structures in their natural position without manipulation, and easy detection of the presence and extent of adhesions. Detection of adhesions is of major importance as they are markers for pelvic inflammatory disease (PID), progressive endometriosis and surgical trauma. Post-inflammatory peritubal adhesions are associated with ampullary mucosal adhesions in 20% of cases rising to 57% where there is distal tubal occlusion. Culdoscopy detects more cases of ovarian endometriosis than laparoscopy. The most frequent site for endometriosis is the caudal pole of the ovary which is visualized at culdoscopy without manipulation avoiding disruption of early adhesion formations. In this small series miniculdoscopy revealed ovarian lesions including hemorrhagic endometriosis, adhesions and fibroma which were not detected at vaginal sonography.

The procedure was remarkably well tolerated by the patients, suggesting that minihydroculdoscopy is likely to be a more suitable outpatient procedure than minilaparoscopy. Discomfort during minilaparoscopy is caused by the $CO_2$ pneumoperitoneum, Trendelenburg position, insertion of an additional trocar, manipulation to remove the bowel from the pelvis and lifting the adnexa to expose the full ovary and fossa ovarica. The pouch of Douglas approach allows a traumatic and full inspection of the ovary, fimbriae and fossa ovarica by moving the optic and without grasping or manipulation of the organs. The movements of the scope in the pelvis were painless. The ease of performing miniculdoscopy opens the possibility of repeat procedures to evaluate the evolution of endometriosis. In addition, the procedure is atraumatic, avoids destruction of early adhesions by manipulation and does not cause peritoneal acidosis.

Obviously, the technique has limitation when compared to laparoscopy. The view at minihydroculdoscopy is limited and restricted to the posterior part of the true pelvis and the gynecologist is more familiar with the panoramic view of the pelvic structures as seen at laparotomy or laparoscopy. It is worth asking whether inspection of the entire abdomen and anterior pelvis is necessary in infertility and, in the absence of tubo-ovarian pathology, whether anything can be gained from abdominal inspection beyond what can be seen with minihydroculdoscopy. The range of interventions which can be performed alongside minihydroculdoscopy is more limited than with laparoscopy, however, minor operative procedures such as biopsy and adhesiolysis can still be performed. In addition, the ampullary segment is in the axis of the culdoscope and, with minimal manipulation the infundibulum can be exposed and the ampulla cannulated. Preliminary attempts to perform culdoscopic salpingoscopy were successful. Inspection of the ampullary mucosa has been shown to be more accurate in selecting patients for surgery and assessing the risk of tubal pregnancy in PID than a combination of hysterosalipingogrpahy and laparoscopy. There are also potential therapeutic applications such as GIFT and ZIFT. Minihydroculdoscopy, however, is not a substitute for laparoscopy but can be proposed as a first line procedure which is performed in the early stages of infertility investigation saving a diagnostic laparoscopy in many patients and avoiding delay in the detection of pathology.

The major contraindication is obstruction of the pouch of Douglas by the rectum or a prolapsed tumor, which are routinely excluded by bimanual examination and transvaginal ultrasound. The intraperitoneal location of the Veress needle is controlled by free deeper insertion and, in case of doubt, by the vacuum test and the injection and aspiration of normal saline. Complications of culdoscopy are estimated at 2% and include bleeding at the puncture site, inadvertent puncture of the posterior wall of the uterus, parametrium and ovarian cyst, rectum perforation and peritonitis. Severe and life threatening complications have been very rare. Rectum perforation is usually extraperitoneal and is treated conservatively with antibiotics without major consequences. Transvaginal ovum pick-up procedures carry a low risk of infection which is estimated at 0.4% whether or not vaginal disinfection is performed. One has, however, to be aware of infection particularly in patients with sequelaie of PID, aiming to diagnose the complication accurately and intervene promptly. Culdocentesis in third world countries is accepted as a safe procedure for the diagnosis of ectopic pregnancy.

Patient, physician and health care manager all stand to benefit from the use of minihydroculdoscopy in infertility care. Hysteroscopy can be performed with the same optic as the minihydroculdoscopy, and additional equipment for pneuoperitoneum is not required. The entire procedure including hysteroscopy and dye hydrotubation is easily performed within less than one hour and, with the application of local anesthesia, no extra time is needed for the recovery of the patient. The cost and complexity of the pelvic endoscopic exploration in infertility are therefore greatly reduced.

The pilot study has shown that minihydroculdoscopy allows atraumatic and detailed exploration of the tuboovarian structures in infertile patients without obvious pelvic pathology. The procedure can be combined with hysteroscopy and dye hydrotubation and has the potential of offering the patient a complete and early exploration of the reproductive tract in a painless, safe and cost effective way. Further studies are in progress to evaluate the acceptability, accuracy, risks and benefits in comparison with minilaparoscopy.

In this pilot study the needle technique allowed full inspection of the fimbriae and the ampullary segment, the fossa ovarica and the ovarian surface in all not operated cases. Hydroflotation avoids manipulation of the tuboovarian structures and allows easy identification of filmy adhesions. The procedure including hysteroscopy and chromopertubation is easily performed within 1 hour and with the application of local anesthesia there is no extra time needed for the recovery of the patient. The patient is fully conscious throughout the procedure. The potential benefits for the patient and the physician and for managed care in fertility are obvious. The technique, however, has also limitations. The inspection is restricted to the small pelvis, there is no panoramic view of the pelvic structures and therapeutic interventions are minimal. Therefore the application of needle culdoscopy is not to replace but to screen and select patients for laparoscopic investigation. It can be performed as a comprehensive investigation at the early stage of infertility and avoid delay of laparoscopy in case of pathology. The combination of needle-culdoscopy, hysteroscopy and chromopertubation can simplify the exploration of the genital tractus, reduce the delay and costs of the fertility investigation and for the patient the inconvenience and pain, associated with the exploration, may be reduced to a minimum.

Culdocentesis is also a well established procedure in developing countries for the diagnosis of ectopic pregnancies. The technique of needle-culdoscopy using the same endoscope as for hysteroscopy and by avoiding insufflation has the advantage of reducing the costs and complexity of the procedure which would increase its use in developing countries.

The risk of bowel damage can be avoided in several ways. Firstly, by clinical and sonographic evaluation of the pouch of Douglas. Secondly, if no fluid in the pouch of Douglas is detected, hysteroscopy using saline as distension medium is performed prior to the culdoscopy. Finally, at the time of culdocentesis fluid can be aspirated, and in case of doubt saline can be injected and aspirated. In conclusion, needle-culdoscopy in combination with hydroflotation can be performed in an office setting. The combination of the hysteroscopy, needle-culdoscopy and chromopertubation has the potential of offering the infertile patient an almost complete exploration of the genital tractus in a painless, safe and cost-effective way.

Features of the present invention could also be used in laparoscopy. Due to new smaller size miniscopes, a new type of culdoscopy can now be achieved as described above. By use of miniscopes and saline, this new type of culdoscopy can be performed as a painless office procedure. Other types of fixation systems for the retractor could be provided, such as a balloon, umbrella, screw, etc.

Through a combination of mini- and micro-endoscopes, the technique of culdoscopy and the principle of hydroflotation by use of a physiological solution as a distension medium, access and visualization of the female small pelvis can be achieved in a simply and painless way, in which exploration and possibly treating can be carried out by this method.

To allow this procedure to proceed as smoothly as possible, a single puncture of the Douglas cavity using a needle or trocar, possibly with a spring mechanism, is used. The needle or trocar is surrounded by a shaft, such that the transfer to the shaft takes place gradually and without a sudden change in diameter. After the withdrawal of the needle or trocar, leaving the shaft in place, the mini- or micro-endoscope can be introduced via the shaft into the Douglas cavity. The shaft and/or the mini- or micro-endoscope may be provided with one or more operating channels. There must be at least one channel to allow irrigation with the distension solution. The shaft may have some fixation system at the end to achieve stabilization within the Douglas cavity. A possibility for rinsing can be provided either by one of the channels in the shaft or by small perforations in the distal part of the shaft.

The invention is related to the development of the technical instrumentation required for carrying out needle hydroculdoscopy or miniculdoscopy. The easy applicability of this technique can bring about a real change in the diagnostic exploration of the internal female genitalia and possible operative treatment. Culdoscopy is a technique by which the female small pelvis can be explored by means of an endoscope via the vagina.

Because of the technical developments in the endoscope area, mini and micro endoscopes are now available with a diameter from 0.5 mm to 5 mm. Thanks to the smaller diameter, the visualization of the small pelvis is made possible with a simple puncture of the Douglas cavity, given that the endoscopes are no thicker than a needle. This is where the technique differs from the earlier culdoscopy which required a greater opening to be made in the fornix utero-vaginalis to gain access to the small pelvis with a thicker endoscope of 10 mm or larger. $CO_2$ was used in the past as a distension medium to achieve improved visualization of the organs. This $CO_2$ has the disadvantage of causing extreme irritation to the peritoneum and diaphragm so that a general anesthetic was required for this operation. We propose the use of physiological solution as a distension medium, since it does not irritate the peritoneum and provides better visualization of the organs as well as of deviations such as adhesions, endometritis, etc. The organs as it were float in the water. It is the combination of mini- and micro-endoscopes, culdoscopy and hydro-flotation (the distension medium is a watery solution) which forms a new diagnostic and therapeutic entity: "needle hydroculdoscopy" also called miniculdoscopy.

The present invention has the intention of solving the disadvantages of the earlier investigative measures by making use of mini- and micro-endoscopes, by which access is gained to the pelvis via the fornix utero-vaginalis by means of a simple prick, as in the ordinary puncture, and which avoids irritation of the peritoneum by using physiological fluid. This vaginal route provides the advantage of being less traumatic and low in risk. Moreover, it allows the organs to be inspected in their normal physiological condition.

The advantages of needle hydroculdoscopy are simplicity and the entirely painless course of the intervention. For this reason it can be carried out with completely ambulatory patients, without anesthetic and with no admission to hospital. The simple applicability allows exploration of the tubes and ovaries to be planned very early in the total fertility exploration, whereas with current techniques i.e., laparoscopy, this is left to the end, given the complexity and risk of the latter intervention.

For the needle hydroculdoscopy to proceed as smoothly as possible a suitable instrumentarium needed to be developed. In doing this, the principle is maintained that the Douglas cavity is simply pricked by a needle, Veress needle or trocar surrounded by a shaft, which may be provided with one or several operating channels. The diameter of this needle, Veress needle or trocar, is adapted to the diameter of the shaft so that the material allows a simple puncture. To do this, smooth transfer is required from the needle to the diameter of the shaft, so that the shaft with the needle can be pushed through the fornix utero-vaginalis into the Douglas cavity without a hitch. After withdrawal of the needle a mini- or micro-endoscope (rigid, semi-rigid or flexible) can be inserted through the shaft. For improved fixation in the Douglas cavity this shaft can be provided with a fixation system at the distal end in the form of a balloon, an umbrella system, a screw thread or other. Physiological solution enters the cavity through one of the shaft's or mini- or micro-endoscope's operating channels and further in flow of solution takes place via this channel throughout the entire duration of the intervention. The other operating channels can be used to introduce small instruments or other optical catheters.

By combining mini- or micro-endoscopes with the culdoscopy technique and the principle of hydro-flotation by the use of liquid as a distension medium, a new diagnostic and therapeutic entity is created, needle hydroculdoscopy or miniculdoscopy, characterized by its simple application and ambulant application. A suitable instrumentarium had to be developed for this. The instrumentarium required for introducing the mini- or micro-endoscope easily into the small pelvis, namely into the Douglas cavity, is so characterized that the intervention should be carried out in one single, simple puncture by a needle or trocar system, in which the needle, Veress needle or trocar is surrounded by a shaft and in which the transfer from the needle must take place gradually, so that when the external shaft is pushed into the Douglas cavity there is no resistance from the tissue of the fornix utero-vaginalis. When the needle has been withdrawn, leaving the shaft in place, the mini- or micro-endoscope is introduced.

Both the mini- and micro-endoscope can be provided with one or more operating channels. At least one of these channels is to be used for the introduction of the distension medium. The other channels can be used for introducing small instruments, optical catheters or to make possible the outflow of water so that a rinse can be carried out. The distal end of the shaft can be provided with a fixation system in the form of a balloon, an umbrella system, a screw thread or some other. To make continuous rinsing possible, the shaft may have various small openings or perforations in its distal part.

Figure 8:
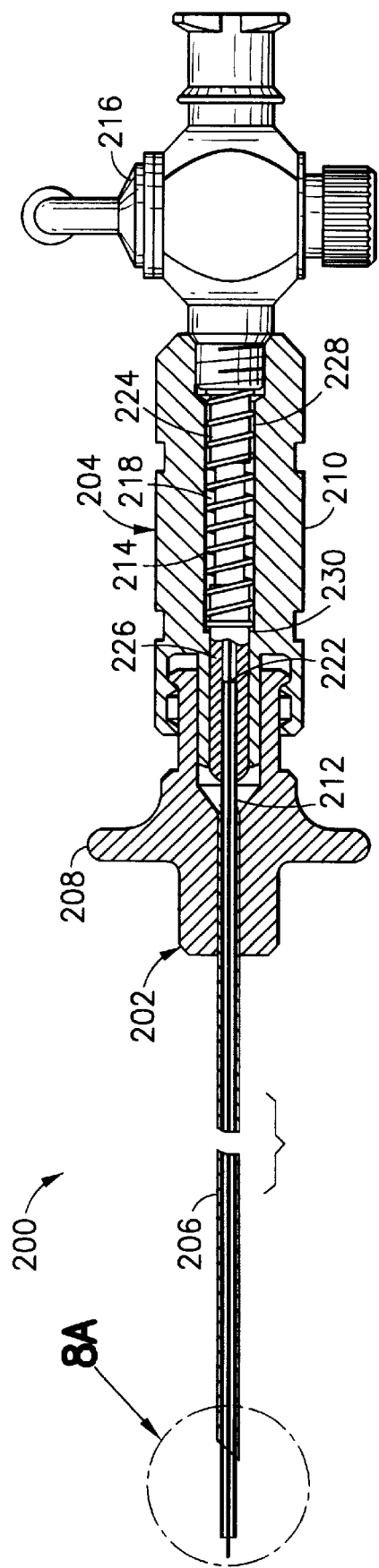
FIG. 8 is a partial cross-sectional view of an alternate embodiment of the Veress needle assembly.
Figure 8A:
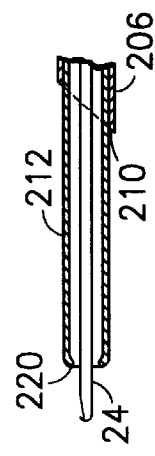
FIG. 8A is an enlarged view of an area 8A in FIG. 8 with a guide wire.

Referring now to FIGS. 8 and 8A, an alternate embodiment of the Veress needle assembly is shown. In this embodiment the Veress needle assembly 200 comprises a hub and needle assembly 202 and a safety obturator assembly 204. The hub and-needle assembly 202 comprises a tubular needle shaft 206 and a hub 208. The front end 210 of the shaft 206 has a needle shaped tip. The hub 208 is attached to the rear end of the shaft 206. The safety obturator assembly 204 comprises a handle 210, an obturator tube 212, a spring loading assembly 214, and a stopcock 216. The handle 210 has a front end which is removably screwed onto the rear end of the hub 208. The stopcock 216 is attached to the rear end of the handle 210. A channel 218 extends through the handle 210 between its front and rear ends. The obturator tube 212 is a one-piece tube with an open front end 220 and an open rear end 222. The diameter of the tube 212 allows it to be slidingly received inside the needle shaft 206. The spring loading assembly 214 is located in the channel 218 and comprises a coil spring 224, an obturator tube extension 226, and a spring stop 228. The tube extension 226 is stationarily attached to the rear end of the obturator tube 212. The tube extension 226 also comprises an outer flange 230. The flange 230 functions as both a spring stop surface for the front of the coil spring 224 and a forward stop surface for stopping forward movement of the tube extension 226 on the handle 210. The rear end of the tube extension 226 is slidingly located inside spring stop 228. The spring stop 228 has a flange that functions as a rear stop surface for the coil spring 224. The spring stop 228 also has a center channel that is aligned with the channel through the tube extension 226 and the channel through the stopcock 216. The spring stop 228 and tube extension 226 are arranged to telescopingly move relative to each other. With this type of embodiment, a guide wire 24 can be passed through the Veress needle assembly 200, from the entrance to the stopcock 216, and out of the open front end 220 of the safety obturator tube 212 after the needle tip 210 has pierced through the peritoneum wall, but without having to remove the safety obturator assembly 204 from the hub and needle assembly 202. With the guide wire 24 in place through the hole in the peritoneum wall, the Veress needle assembly can be removed and the cannula and dilating obturator inserted through the hole over the guide wire similar to that shown in FIGS. 2D and 2E. In one system of the present invention, the two different types of Veress needle assemblies 200 (FIG. 8) and 18 (FIG. 2A) can be alternatively used with the same dilating obturator and cannula.

Figure 9:
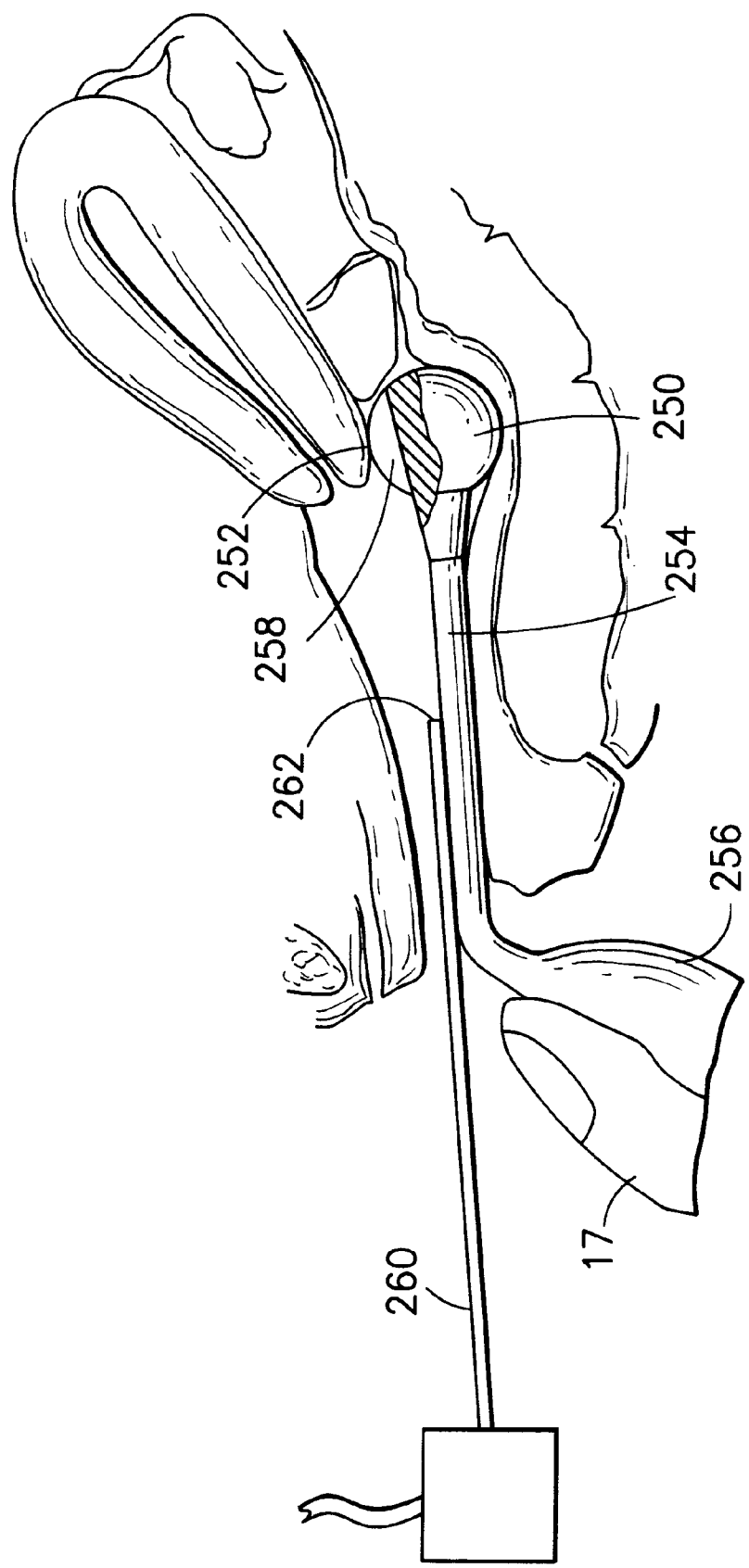
FIG. 9 is a schematic view of a guide and an ultrasound probe being inserted into a patient.

Referring now to FIG. 9, another feature of the guide will be described. In this embodiment, the guide 250 is substantially similar to the guide 10 shown in FIG. 2A. The guide 250 comprises a leading end 252, a shaft 254, and a user contacting rear end 256. The leading end 252 is sized and shaped to seat in the vagina next to the cervix and adjacent the peritoneum wall. The leading end 252 has a guide slot 258 therethrough. The guide 250 is shown in place in the vagina and an ultrasound probe 260 is shown being placed into the guide. In this embodiment the guide slot 258 is sized and shaped to receive the front end 262 of the probe 260 and position the front end 262 against the peritoneum wall. Thus, the guide 250 is used to relatively quickly and stably locate the front end 262 at a predetermined general location against the peritoneum wall in the vagina. A user can, thus, get an ultrasound picture of the area behind the peritoneum wall; perhaps in preparation of using the tissue penetrating instrumentation. The guide could also be used with other instruments.

Referring now to FIGS. 10A and 10B, another embodiment of the present invention is shown. In this embodiment, the system is similar to the system shown in FIG. 3A and comprises a guide 270, a Veress needle assembly 272, a dilating obturator 274, a cannula 276, and a mechanism 278 for moving the Veress needle assembly 272 forward relative to the guide 270. The guide 270 has a rear section 280 that houses the mechanism 278. One example of the mechanism 278 comprises a spring 282, a movement section 284, and a user actuated release 286. The movement section 284 is movably mounted to the rear section 280 and is adapted to engage or interlock with the hub 288 of the Veress needle 272. The movement section 284 is movable between a cocked position shown in FIG. 10A and a released position shown in FIG. 10B. In the cocked position shown in FIG. 10A the Veress needle assembly 272 is located in a reward position relative to the guide 270 with the front tip of the Veress needle assembly located behind the front tip of the guide. The spring 282 is compressed. The release 286 is in an interlocking retaining position with the movement section 284. After the front end of the guide 270 is positioned against the peritoneum wall, the user presses down on the release 286 as indicated by arrow G. This causes the release 286 to disengage from the movement section 284. As seen from comparing FIGS. 10A and 10B, the spring 282 then propels the movement section 284 forward as indicated by arrow H which, in turn, propels the hub 288 and the rest of the Veress needle assembly 272 forward at a high rate of speed. Preferably, the guide 270 has a stop to stop the forward movement of the Veress needle assembly 272 when the front of the assembly projects forward a predetermined distance A. With this type of instrument, there will be less pain or discomfort to the patient because of the high velocity puncture. In addition, the limited forward range of movement of the Veress needle assembly helps to insure that the assembly will not be inserted too deeply past the peritoneum wall; thereby reducing risk of damage to tissue behind the peritoneum wall.

Referring now to FIGS. 11A and 11B, an alternate embodiment of a dilating obturator with cutting means is shown. In this embodiment the obturator 300 has a front cone section 302, a shaft section 304, a front aperture 306, and cutting means 308. One example of a cutting means is bladed cutting elements as shown. The instrument could alternatively or additionally incorporate other types of surgical cutting means, such as monopolar or bipolar electrodes or laser ports. The Veress needle assembly 310 projects out of the front aperture 306. The cone section 302 has slots therethrough. The cutting blades 308 are movable relative to the frame of the obturator to move from a position recessed in the slots (FIG. 11A) to a position extended from the slots (FIG. 11B). With this type of embodiment, the Veress needle assembly 310 will make the initial hole through the peritoneum wall. As the obturator 300 is advanced, the blades 308 are extended to cut slots at sides of the hole. The obturator 300 is further advanced with the cone section 302 widening the hole. The blades 308 are retracted as the cone section 302 passes through the hole to prevent inadvertent damage to tissue behind the peritoneum wall.

Referring now to FIGS. 12A, 12B and 12C, another feature of the present invention is shown. The system comprises the Veress needle assembly 200 having the stopcock 216 and a pressure signaler 400. One example of a pressure signaler 400 comprises a frame 402 and a thin wall elastomeric bladder 404. The frame 402 has vent holes 406 and a front end 408 that is removably attached to the rear end of the stopcock 216. The signaler 400 is attached to the Veress needle assembly before penetration through the peritoneum wall. The gas pressure behind the peritoneum wall is less than atmospheric pressure; slightly negative at 1 to 3 millibars. When the front tip of the Veress needle assembly penetrates the peritoneum wall, and the stopcock valve is opened as seen in FIG. 12C, the negative pressure causes air to flow from the bladder through Veress needle assembly to the needle tip. This causes the bladder 404 to collapse thereby signaling to the user that the tip of the Veress needle assembly is properly positioned. If the tip of the Veress needle assembly was not properly positioned, such as being in the uterus or colon, the bladder 404 would not collapse. In alternate embodiments, other types of pressure signalers 400 could be provided, such as an electronic pressure transducer or an analog gage. Alternatively, no pressure signaler or pressure change signaler need be provided.

Figure 13A:
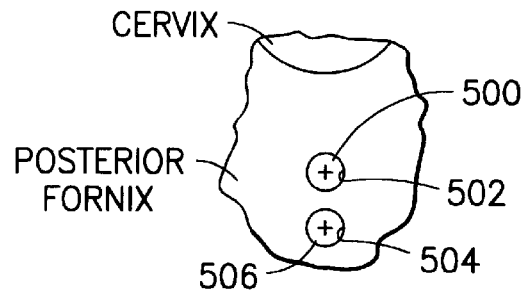
FIG. 13A is a partial schematic view of the posterior fornix of a patient having two separate holes with a telescope and a separate working instrument located in the separate holes.
Figure 14A:
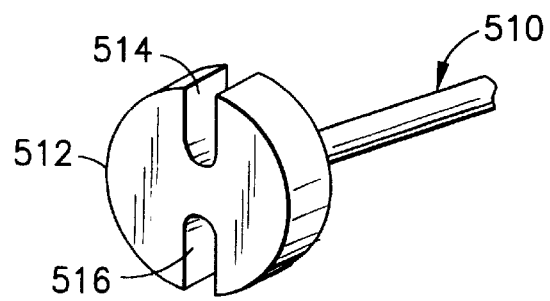
FIG. 14A is a perspective view of a front end of a Veress needle guide for making the two holes shown in FIG. 13A.
Figure 14B:
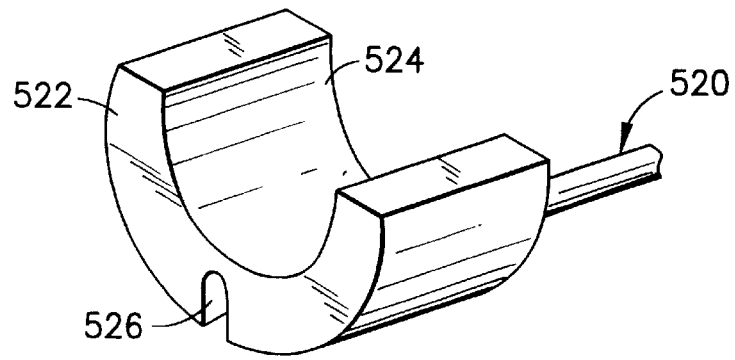
FIG. 14B is a perspective view of a front end of another alternate embodiment of the Veress needle guide.

Referring now to FIG. 13A a method will be described that uses more than one puncture through the vaginal and peritoneal walls at the posterior fornix. In this method an endoscope 500 is inserted through a hole 502 by any of the methods described above. Then, a separate hole 504 is punctured into the pouch of Douglas in close proximity to the first hole 502. A working instrument 506 is passed through the second hole 504. Any suitable type of working instrument could be used, such as a biopsy needle. Thus, the present invention allows a surgeon the ability to not only make visual observations, but also perform surgical tasks while the endoscope is in position. Referring also to FIG. 14A, the front end of a Veress needle guide 510 is shown for use with this type of dual penetration method. The front end 512 has two guide channels 514, 516. The upper guide channel 514 is used with a Veress needle to make the first penetration that eventually becomes the first hole 502. The lower guide channel 516 is used with a Veress needle to make the second penetration that eventually becomes the second hole 504. In an alternate embodiment, as shown in FIG. 14B, a guide 520 can be used to make the working instrument hole 504 after the endoscope 500 has been positioned. In this embodiment the guide 520 has a front end 522 with an upper slot 524 and a lower slot 526. The upper slot 524 is sized and shaped to seat against the endoscope 500. The lower slot 526 is sized and shaped to receive a Veress needle. Thus, the guide 520 can be placed against the endoscope or cannula, already extending into the pouch of Douglas, and allow a second puncture to be made in a precise distance and location relative to the endoscope.

Figure 13B:
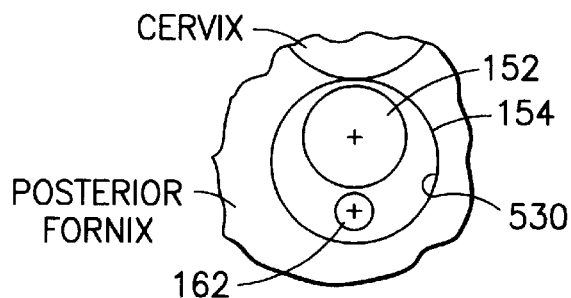
FIG. 13B is a partial schematic view of the posterior fornix of a patient having a single hole with an instrument therein having a telescope and a working instrument.

Referring now to FIGS. 13B and 7D another method of locating both a telescope and a working instrument can be accomplished with use of only a single penetration. In this method a single widened hole 530 is formed as described above by initially using a Veress needle. The endoscope in this embodiment has the working sheath 154, the telescope 152, and the forceps 162. The front end 163 of the forceps 162 can be extended past the front end 155 of the working sheath 154. The front end of the telescope is located at the front end 155 of the working sheath 154. Thus, both the telescope and working instrument can be passed through a single hole. Alternatively, an endoscope with integral irrigation and accessory channel(s) could be used with or without an over sheath through the single puncture site.

Figure 15:
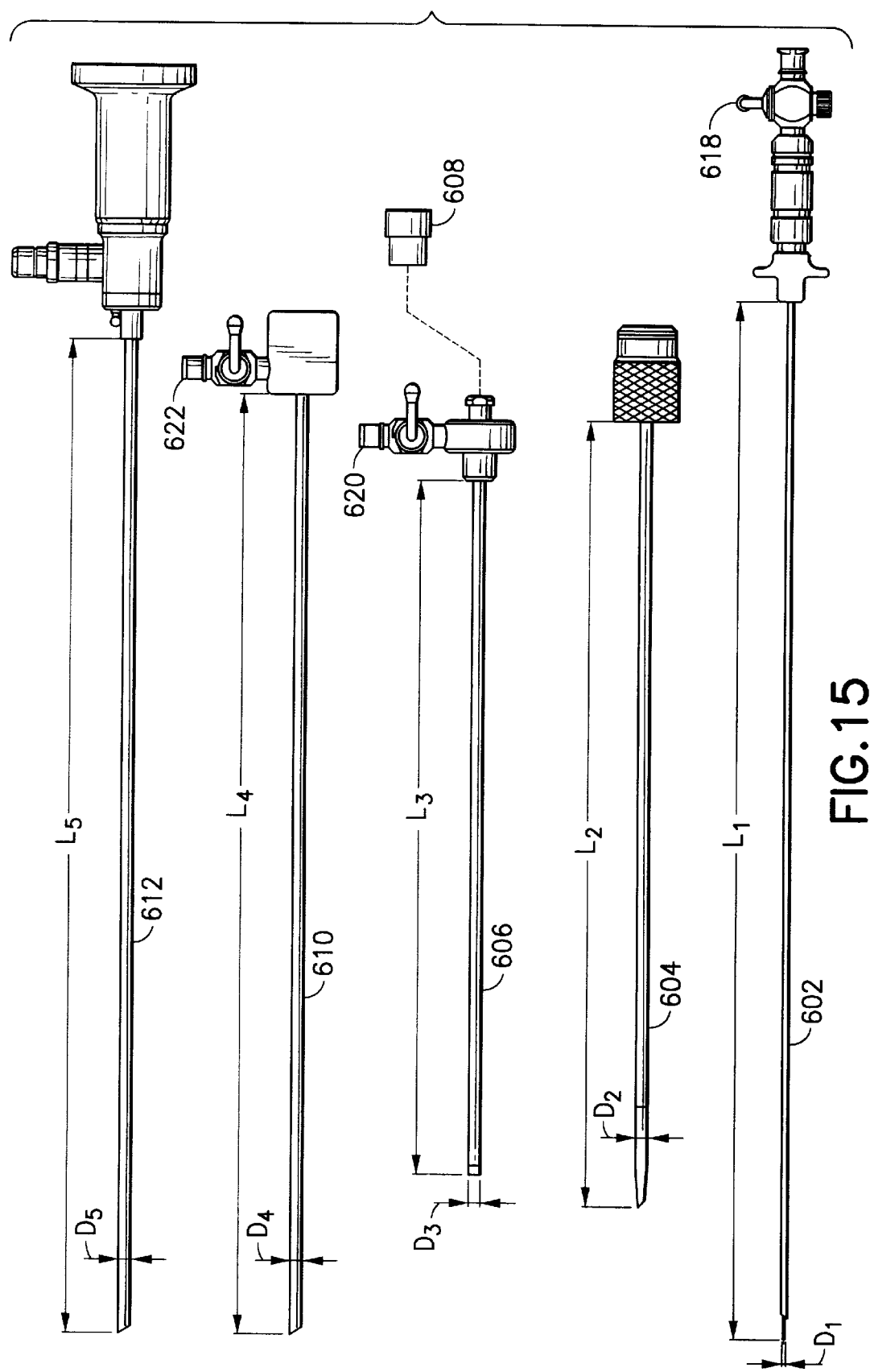
FIG. 15 is an elevational side view of components of a transvaginal hydrolaparoscope system.

Referring now to FIG. 15 components of a transvaginal hydrolaparoscopy system are shown. The system comprises a Veress needle 602, an obturator 604, a cannula 606, a seal 608, a sheath 610, a telescope 612, and an optional guidewire (not shown). The Veress needle 602, obturator 604 and cannula 606 are combined into an assembly 614 as seen in FIG. 16. Likewise, the sheath 610 and telescope 612 can be combined into an assembly 616 as seen in FIG. 17. Now, referring to FIG. 15., in this embodiment the length $L_1$ of the Veress needle shaft and its safety obturator tip is about 250 mm and the diameter $D_1$ is about 1.6 mm. The length $L_2$ of the shaft of the obturator 604 is about 208 mm and the diameter $D_2$ is about 3.6 mm. The length $L_3$ of the shaft of the cannula 606 is about 175 mm and the diameter $D_3$ is about 4.2 mm. The shaft of the sheath 610 has a length $L_4$ of about 245 mm and a diameter $D_4$ of about 3.5 mm. The shaft of the telescope 612 has a length $L_5$ of about 260 mm and a diameter $D_5$ of about 2.7 mm. However, other dimensions could be provided. The Veress needle 602, cannula 606 and sheath 610 also have stopcocks 618, 620, 622.

Figure 18:
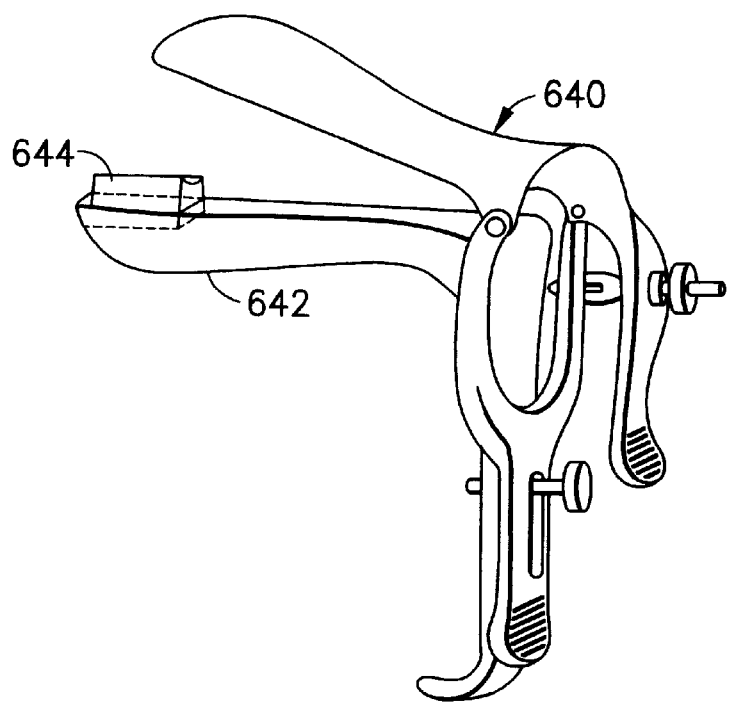
FIG. 18 is a perspective view of a combined speculum and Veress needle guide apparatus.
Figure 19:
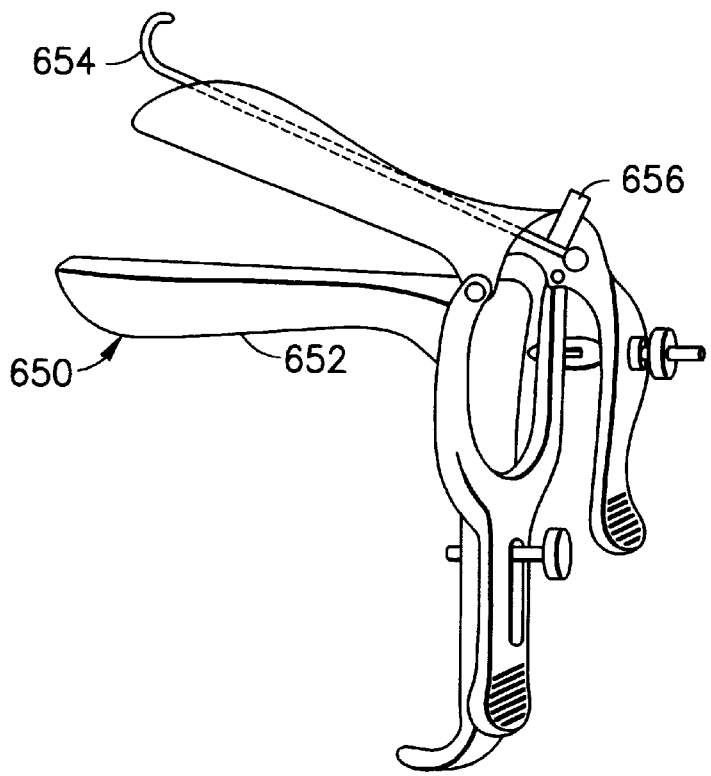
FIG. 19 is a perspective view of a combined speculum and tenaculum apparatus.
Figure 20:
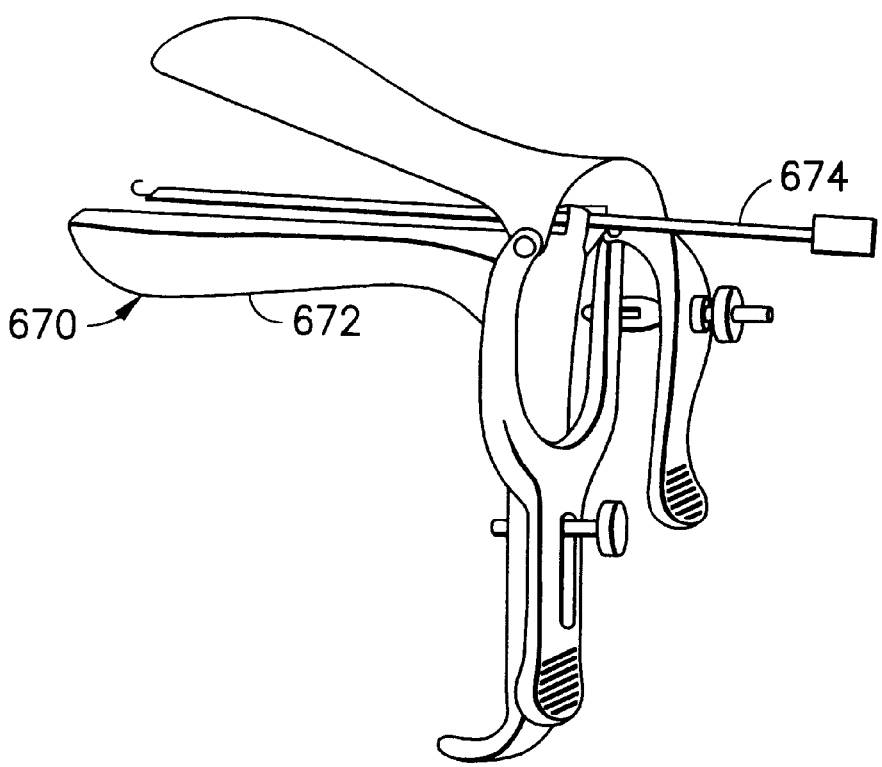
FIG. 20 is a perspective view of a combined speculum and Veress needle apparatus.
Figure 21:
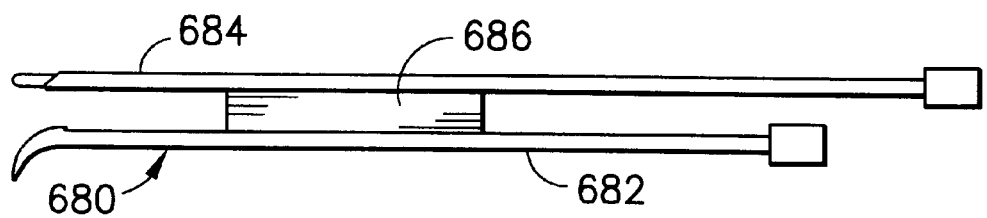
FIG. 21 is an elevational side view of a combined tenaculum and Veress needle assembly.

Referring now to FIG. 18 a combined speculum and Veress needle guide apparatus 640 is shown. The apparatus 640 comprises a speculum section 642 and a Veress needle guide section 644. Thus, the Veress needle guide feature can be integrated into a speculum. The guide section 644 could be removably mounted to the speculum section 642. Referring now to FIG. 19 a combined speculum and tenaculum apparatus 650 is shown. The apparatus 650 has a speculum section 652 and a tenaculum section 654. The tenaculum section 654 is movably attached to the speculum section 652 and preferably has a locking mechanism 656 to lock their relative positions. The front tip of the tenaculum can be used to grasp the uterus and pull the posterior fornix taut. Referring now to FIG. 20, a combined speculum and Veress needle apparatus 670 is shown. The apparatus 670 has a speculum section 672 and a Veress needle section 674. The needle section 674 is removably mounted to the speculum section and is adapted to longitudinally axially move relative to the speculum section 672. Referring now to FIG. 21, a combined tenaculum and Veress needle apparatus 680 is shown. The apparatus 680 has a tenaculum section 682 and a Veress needle section 684. The Veress needle section 684 is movably mounted to the tenaculum section 682 on a guide section 686 which allows restrained longitudinal axial movement of the Veress needle section 684 relative to the tenaculum section 682. The various embodiments shown in FIGS. 18–21 illustrate that instruments such as a Veress needle, a Veress needle guide, a speculum, a tenaculum, or other instruments can be attached and combined to allow a doctor to have greater and easier overall control.

Figure 22:
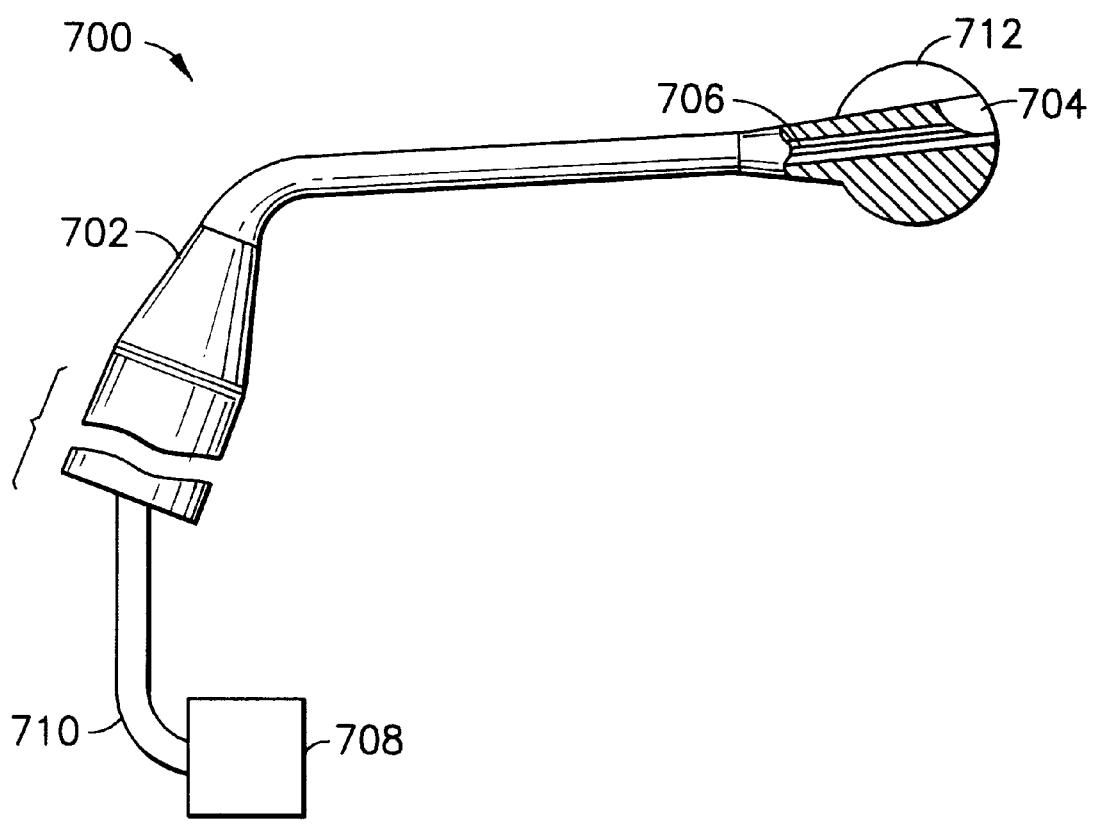
FIG. 22 is a schematic elevational side view with a cut-away section of a combined Veress needle guide and ultrasound probe apparatus.

Referring now to FIG. 22, a combined Veress needle guide and ultrasound probe apparatus 700 is shown. The apparatus 700 generally comprises a frame 702, an ultrasound probe tip 704, electrical wires 706, an ultrasound base unit 708 and a cable 710 connecting the wires 706 to the base unit 708. The frame 702 has a front end with a Veress needle guide channel 712. The probe tip 704 is mounted to the frame 702 at the front of the front end to contact the posterior fornix. The wires 706 connect the probe tip 704 to the base unit 708 through a frame 702 and with the cable 710. With this type of device the doctor can view an ultrasound picture of the area behind the posterior fornix before and during penetration with a Veress needle and, with a predetermined viewing position relative to the path of the Veress needle as limited by the guide channel 712.

It should be understood that the foregoing description is only illustrative of the invention. Various alternatives and modifications can be devised by those skilled in the art without departing from the present invention. Accordingly, the present invention is intended to embrace all such alternatives, modifications and variances which fall within the scope of the appended claims.

What is claimed is:

1. A medical instrument guide comprising:
    a leading end having a general rounded blunt shape and a guide channel therethrough, the leading end being sized and shaped to seat in a posterior fornix of a vagina of a patient, wherein the rounded blunt shape of the leading end can be pushed against tissue at the posterior fornix to tighten the tissue without piercing through the tissue;
    a shaft extending from the leading end; and
    a rear end connected to the shaft which is sized and shaped to be held and manipulated by the user;
    wherein the guide can be inserted into the patient's vagina and positioned against the posterior fornix such that medical instrument can be inserted through the guide channel to a position against the vaginal wall below the patient's cervix, wherein the guide channel is a slot extending into the leading end from a top surface of the leading end.

2. A guide as in claim 1 further comprising an ultrasound probe tip located at the leading end of the guide.

3. A guide as in claim 1 further comprising a stop for preventing the medical instrument from advancing past a front of the leading end a predetermined distance.

4. A guide as in claim 3 wherein the medical instrument is a Veress needle and the predetermined distance is about 15 mm.

5. A medical instrument guide comprising:
    a leading end having a general rounded blunt shape and a guide channel therethrough, the leading end being sized and shaped to seat in a posterior fornix of a vagina of a patient, wherein the rounded blunt shape of the leading end can be pushed against tissue at the posterior fornix to tighten the tissue without piercing through the tissue;
    a shaft extending from the leading end; and
    a rear end connected to the shaft which is sized and shaped to be held and manipulated by the user;
    wherein the guide can be inserted into the patient's vagina and positioned against the posterior fornix such that a medical instrument can be inserted through the guide channel to a position against the vaginal wall below the patient's cervix, wherein the guide has a section for removably mounting the guide to a cannula.

6. A medical instrument guide comprising:
    a leading end having a general rounded blunt shape and a guide channel therethrough, the leading end being sized and shaped to seat in a posterior fornix of a vagina of a patient, wherein the rounded blunt shape of the leading end can be pushed against tissue at the posterior fornix to tighten the tissue without piercing through the tissue;
    a shaft extending from the leading end; and
    a rear end connected to the shaft which is sized and shaped to be held and manipulated by the user;
    wherein the guide can be inserted into the patient's vagina and positioned against the posterior fornix such that a medical instrument can be inserted through the guide channel to a position against the vaginal wall below the patient's cervix, wherein the leading end has a top surface with a recess to accommodate the cervix.

7. A method of inserting a cannula through a peritoneum wall of a patient comprising steps of:
    inserting a Veress needle assembly into a vagina of the patient and through the peritoneum wall to form a hole in the peritoneum wall;
    expanding the size of the hole; and
    sliding the cannula into the expanded size hole.

8. A method as in claim 7 wherein the step of expanding the size of the hole comprises a tubular frame piece of the Veress needle assembly having a first section with a first diameter, a second section with a larger second diameter, and a dilating expanding section between the first and second sections, wherein the step of expanding comprises the dilating section expanding the size of the hole as the tubular frame piece is passed through the hole.

9. A method as in claim 7 wherein the step of expanding the size of the hole comprises sliding a dilating obturator over the Veress needle assembly through the hole and thereby wedging the hole wider.

10. A method as in claim 9 wherein the step of sliding the cannula slides the cannula over the dilating obturator into the hole.

11. A method as in claim 7 further comprising inserting a guide wire through the Veress needle assembly and out a front end of the Veress needle assembly.

12. A method as in claim 11 further comprising removing the Veress needle assembly from the peritoneum wall and the vagina while the guide wire stays in the hole.

13. A method as in claim 12 wherein the step of expanding comprises inserting a dilating obturator over the guide wire and into the hole and wedging the hole wider.

14. A method as in claim 13 wherein the step of expanding the size of the hole comprises lateral cutters on the dilating obturator cutting slits on the sides of the hole.

15. A method as in claim 14 wherein the cutters comprise blades that are moved between extended and retracted positions on the dilating obturator.

16. A method as in claim 7 further comprising inserting a guide into the vagina, the guide having a guide slot therein, wherein the step of inserting the Veress needle assembly comprises placing the Veress needle assembly into the guide slot of the guide.

17. A method as in claim 7 wherein the step of inserting the Veress needle assembly comprises actuating a drive mechanism on a guide to insert the Veress needle assembly through the peritoneum wall at high velocity.

18. A method as in claim 17 wherein the step of actuating comprises releasing a compressed spring and the step of inserting further comprises limiting forward motion of the Veress needle assembly relative to the guide to a predetermined position.

19. A method as in claim 7 further comprising determining if a needle tip of the Veress needle assembly has properly penetrated the peritoneum wall by sensing a change in gas pressure at the needle tip and signaling a user of the change in gas pressure.

20. A method of inserting a cannula through tissue of a patient comprising steps of:
  inserting a Veress needle assembly into the tissue of the patient to form a hole in the tissue;
  expanding the size of the hole by passing a dilating obturator into the hole, the dilating obturator having a front end with a tapered shape with an expanding outside dimension along a length of the front end; and
  sliding the cannula over the dilating obturator into the expanded size hole,
  wherein the step of inserting the Veress needle assembly into the tissue of the patient comprises inserting the Veress needle assembly into a vagina of the patient.

21. A method as in claim 20 further comprising guiding positioning of the Veress needle assembly relative to the tissue before insertion through the tissue by a hand-held guide having the Veress needle assembly thereon.

22. A method as in claim 21 wherein the guide comprises an ultrasound probe tip and the step of guiding comprises a user viewing an ultrasound picture generated from the ultrasound probe tip.

23. A method as in claim 20 wherein the step of inserting comprises piercing through a peritoneum wall of the patient below the patient's cervix.

24. A method of inserting a telescope into a patient comprising steps of:
  inserting a cannula into the patient as recited in claim 20;
  removing the Veress needle assembly and the dilating obturator from inside the cannula; and
  inserting the telescope through the cannula into the patient.

25. A method of inserting a cannula through tissue of a patient, the method comprising steps of:
  forming a passageway through the tissue;
  expanding the size of the passageway by sliding a dilating member through the passageway; and
  sliding the cannula over the dilating member to position the cannula through the expanded size passageway,
  wherein the tissue comprises a peritoneum wall of the patient, and wherein the steps of forming the passageway comprises forming the passageway through the peritoneum wall at a vagina of the patient, and wherein the cannula is slid through the vagina.

* * * * *